(12) United States Patent
Spencer

(10) Patent No.: US 9,272,009 B2
(45) Date of Patent: Mar. 1, 2016

(54) METHOD FOR INCREASING PERFORMANCE OF OFFSPRING

(71) Applicant: JBS United, Inc., Sheridan, IN (US)

(72) Inventor: Joel Dean Spencer, Westfield, IN (US)

(73) Assignee: JBS United, Inc., Sheridan, IN (US)

( * ) Notice: Subject to any disclaimer, the term of this patent is extended or adjusted under 35 U.S.C. 154(b) by 0 days.

(21) Appl. No.: 14/804,992

(22) Filed: Jul. 21, 2015

(65) Prior Publication Data

US 2016/0000119 A1    Jan. 7, 2016

Related U.S. Application Data

(60) Continuation of application No. 13/784,111, filed on Mar. 4, 2013, which is a division of application No. 12/950,620, filed on Nov. 19, 2010, now Pat. No. 8,409,585, which is a continuation of application No. 12/738,154, filed as application No. PCT/US2008/079995 on Oct. 15, 2008, now abandoned.

(60) Provisional application No. 60/980,143, filed on Oct. 15, 2007.

(51) Int. Cl.
*A61K 36/00* (2006.01)
*A61K 36/02* (2006.01)

(52) U.S. Cl.
CPC ..................................... *A61K 36/02* (2013.01)

(58) Field of Classification Search
None
See application file for complete search history.

(56) References Cited

U.S. PATENT DOCUMENTS

| | | | |
|---|---|---|---|
| 2,800,457 A | 7/1957 | Green et al. |
| 3,966,998 A | 6/1976 | Rawlings et al. |
| 4,001,411 A | 1/1977 | Seubert et al. |
| 4,113,867 A | 9/1978 | Seubert et al. |
| 4,141,978 A | 2/1979 | Seubert et al. |
| 4,196,291 A | 4/1980 | Seubert et al. |
| 4,211,795 A | 7/1980 | Leroy et al. |
| 4,593,647 A | 6/1986 | Sorgeloos et al. |
| 4,639,444 A | 1/1987 | Fujikawa et al. |
| 4,752,618 A | 6/1988 | Mascioli et al. |
| 4,764,532 A | 8/1988 | Corman et al. |
| 4,774,232 A | 9/1988 | Szejtli et al. |
| 4,792,546 A | 12/1988 | Baker |
| 4,868,001 A | 9/1989 | Maruta |
| 4,960,795 A | 10/1990 | Salte et al. |
| 4,981,105 A | 1/1991 | Petersen |
| 5,023,100 A | 6/1991 | Chang et al. |
| 5,053,234 A | 10/1991 | Anderson et al. |
| 5,075,231 A | 12/1991 | Moreau et al. |
| 5,098,573 A | 3/1992 | Huckins et al. |
| 5,110,592 A | 5/1992 | Stitt |
| 5,110,731 A | 5/1992 | Fisher |
| 5,113,755 A | 5/1992 | Anderson et al. |
| 5,132,118 A | 7/1992 | Mills |
| 5,141,755 A | 8/1992 | Weisman |
| 5,162,129 A | 11/1992 | Anderson et al. |
| 5,324,521 A | 6/1994 | Gertner et al. |
| 5,332,577 A | 7/1994 | Gertner et al. |
| 5,340,577 A | 8/1994 | Nisbet et al. |
| 5,397,591 A | 3/1995 | Kyle et al. |
| 5,439,924 A | 8/1995 | Miller |
| 5,478,557 A | 12/1995 | Nisbet et al. |
| 5,492,938 A | 2/1996 | Kyle et al. |
| 5,502,077 A | 3/1996 | Breivik et al. |
| 5,532,002 A | 7/1996 | Story |
| 5,571,522 A | 11/1996 | Munson et al. |
| 5,609,880 A | 3/1997 | Munson et al. |
| 5,670,191 A | 9/1997 | Cummings et al. |
| 5,698,246 A | 12/1997 | Villamar |
| 5,728,719 A | 3/1998 | Miller |
| 5,738,871 A | 4/1998 | Story |
| 5,747,533 A | 5/1998 | Egberg et al. |
| 5,798,112 A | 8/1998 | Heitz et al. |
| 5,834,473 A | 11/1998 | Virtanen et al. |
| 5,869,530 A | 2/1999 | Ponroy |
| 5,869,714 A | 2/1999 | Bruzzese |
| 5,876,780 A | 3/1999 | Virtanen et al. |
| 5,876,995 A | 3/1999 | Bryan |
| 5,951,977 A | 9/1999 | Nisbet et al. |
| 5,985,348 A | 11/1999 | Barclay |
| 6,015,798 A | 1/2000 | Ogilvie et al. |
| 6,020,377 A | 2/2000 | O'Quinn et al. |
| 6,060,087 A | 5/2000 | Cook et al. |

(Continued)

FOREIGN PATENT DOCUMENTS

| EP | 1169924 | 1/2002 |
|---|---|---|
| JP | 2004065002 | 3/2004 |

(Continued)

OTHER PUBLICATIONS

Morrison, F.B., "Feeds and Feeding, A Handbook for the Student and Stockman", The Morrison Publishing Company, pp. 602-604, (1954).
Ensminger, M.E., "The Stockman's Handbook", The Interstate, pp. 401-406, (1978).
Fritsche, et al., "Enrichment of Omega-3 Fatty Acids in Suckling Pigs by Maternal Dietary Fish Oil Supplementation", J. Anim. Sci., 71: 1841-1847, (1993).
Allen, et al., "Association of Lowered Plasma Carotenoids with Protection Against Cecal Coccidiosis by Diets High in n-3 Fatty Acids", Poultry Science, 75: 966-972, (1996).

(Continued)

*Primary Examiner* — Qiuwen Mi
(74) *Attorney, Agent, or Firm* — Barnes & Thornburg LLP

(57) ABSTRACT

Methods and compositions for increasing intestinal transport of nutrients or growth performance in the offspring of an animal are described. More specifically, a feed composition comprising an omega-3 fatty acid-containing composition for increasing intestinal transport of nutrients or growth performance in the offspring of the animal, and methods therefor, are described.

14 Claims, 9 Drawing Sheets

(56) References Cited

U.S. PATENT DOCUMENTS

| | | | |
|---|---|---|---|
| 6,068,976 | A | 5/2000 | Briggs et al. |
| 6,086,878 | A | 7/2000 | Adalsteinsson et al. |
| 6,113,886 | A | 9/2000 | Bryan |
| 6,152,358 | A | 11/2000 | Bryan |
| 6,190,720 | B1 | 2/2001 | Yuan et al. |
| 6,207,856 | B1 | 3/2001 | Veech |
| 6,280,755 | B1 | 8/2001 | Berger et al. |
| 6,316,038 | B1 | 11/2001 | Veech |
| 6,323,237 | B1 | 11/2001 | Veech |
| 6,372,460 | B1 | 4/2002 | Gladue et al. |
| 6,391,620 | B1 | 5/2002 | Olivier |
| 6,429,198 | B1 | 8/2002 | St. Cyr et al. |
| 6,432,468 | B1 | 8/2002 | Akimoto et al. |
| 6,441,036 | B1 | 8/2002 | Berge |
| 6,566,583 | B1 | 5/2003 | Facciotti et al. |
| 6,576,819 | B1 | 6/2003 | Leustek |
| 6,579,713 | B2 | 6/2003 | Olivier |
| 6,608,222 | B2 | 8/2003 | Bonsignore et al. |
| 6,610,868 | B2 | 8/2003 | Saebo et al. |
| 6,613,802 | B1 | 9/2003 | Luskey et al. |
| 6,623,776 | B1 | 9/2003 | Wathne et al. |
| 6,624,194 | B1 | 9/2003 | Luskey et al. |
| 6,632,291 | B2 | 10/2003 | Rabon et al. |
| 6,656,494 | B1 | 12/2003 | Nakata et al. |
| 6,723,897 | B2 | 4/2004 | Brown et al. |
| 6,753,350 | B1 | 6/2004 | Hansen et al. |
| 6,812,009 | B2 | 11/2004 | Gladue et al. |
| 6,822,142 | B2 | 11/2004 | Karunanandaa et al. |
| 7,001,610 | B2 | 2/2006 | Stewart |
| 7,015,249 | B1 | 3/2006 | Vanden Heuvel et al. |
| 7,084,175 | B2 | 8/2006 | Wilson et al. |
| 7,115,297 | B2 | 10/2006 | Stillman |
| 7,195,917 | B2 | 3/2007 | Brown et al. |
| 7,214,853 | B2 | 5/2007 | Facciotti et al. |
| 8,409,585 | B2 | 4/2013 | Spencer |
| 2001/0014696 | A1 | 8/2001 | Veech |
| 2001/0041736 | A1 | 11/2001 | Veech |
| 2001/0046493 | A1 | 11/2001 | Margolin et al. |
| 2002/0012689 | A1 | 1/2002 | Stillman |
| 2002/0051844 | A1 | 5/2002 | Wilson et al. |
| 2002/0147356 | A1 | 10/2002 | Bonsignore et al. |
| 2003/0017144 | A1 | 1/2003 | Margolin et al. |
| 2003/0022937 | A1 | 1/2003 | Veech |
| 2003/0060509 | A1 | 3/2003 | Elswyk et al. |
| 2003/0064104 | A1 | 4/2003 | Stillman |
| 2003/0070674 | A1 | 4/2003 | Perry et al. |
| 2003/0072787 | A1 | 4/2003 | Wilson et al. |
| 2003/0150008 | A1 | 8/2003 | Karunanandaa et al. |
| 2003/0198730 | A1 | 10/2003 | Stewart |
| 2003/0220399 | A1 | 11/2003 | Luskey et al. |
| 2004/0039053 | A1 | 2/2004 | Luskey et al. |
| 2004/0044079 | A1 | 3/2004 | Sunvold et al. |
| 2004/0128705 | A1 | 7/2004 | Murray et al. |
| 2004/0171671 | A1 | 9/2004 | Veech |
| 2004/0176320 | A1 | 9/2004 | Natunen et al. |
| 2004/0202769 | A1 | 10/2004 | Stewart |
| 2004/0266872 | A1 | 12/2004 | Veech |
| 2005/0079232 | A1 | 4/2005 | Offord-Cavin et al. |
| 2005/0085451 | A1 | 4/2005 | Carr |
| 2005/0086713 | A1 | 4/2005 | Karunanandaa et al. |
| 2005/0118299 | A1 | 6/2005 | Vickers et al. |
| 2005/0119222 | A1 | 6/2005 | Norton et al. |
| 2005/0154064 | A1 | 7/2005 | Piomelli et al. |
| 2005/0159483 | A1 | 7/2005 | Bassaganya-Riera |
| 2005/0165105 | A1 | 7/2005 | Bassaganya-Riera |
| 2005/0234099 | A1 | 10/2005 | Bertinato et al. |
| 2005/0255145 | A1 | 11/2005 | Macgregor et al. |
| 2005/0267100 | A1 | 12/2005 | Elliott et al. |
| 2005/0282897 | A1 | 12/2005 | Vanden Heuvel et al. |
| 2006/0014717 | A1 | 1/2006 | Angstrom et al. |
| 2006/0122148 | A1 | 6/2006 | Teneberg et al. |
| 2006/0128587 | A1 | 6/2006 | Margolin et al. |
| 2006/0205815 | A1 | 9/2006 | Patel |
| 2006/0217385 | A1 | 9/2006 | Edwards et al. |
| 2006/0223851 | A1 | 10/2006 | Bertinato et al. |
| 2007/0009576 | A1 | 1/2007 | Stillman |
| 2007/0037885 | A1 | 2/2007 | Edwards |
| 2007/0082008 | A1 | 4/2007 | Harel et al. |
| 2007/0082063 | A1 | 4/2007 | Bibus et al. |
| 2007/0093525 | A1 | 4/2007 | Bertinato et al. |
| 2007/0098822 | A1 | 5/2007 | Mankovitz |
| 2007/0202194 | A1 | 8/2007 | Kiliaan et al. |
| 2010/0323028 | A1 | 12/2010 | Webel et al. |
| 2011/0256170 | A1 | 10/2011 | Spencer |
| 2013/0184349 | A1 | 7/2013 | Spencer |

FOREIGN PATENT DOCUMENTS

| | | |
|---|---|---|
| WO | WO 98/00125 | 1/1998 |
| WO | WO 99/08540 | 2/1999 |
| WO | WO 01/28354 | 4/2001 |
| WO | WO 01/91575 | 12/2001 |
| WO | 03/017945 | 3/2003 |
| WO | 2004/009826 | 1/2004 |
| WO | WO 2004/032918 | 4/2004 |
| WO | 2004/080196 | 9/2004 |
| WO | 2004/095940 | 11/2004 |
| WO | 2007/117511 | 10/2007 |
| WO | 2009/052182 | 4/2009 |
| WO | 2009/070589 | 6/2009 |

OTHER PUBLICATIONS

Arbuckle, et al., "Docosahexaenoic Acid is Transferred through Maternal Diet to Milk and to Tissues of Natural Milk-Fed Piglets", J. Nutr., pp. 1668-1675, (1993).

Belne, Margaret, "Dietary Fish Oil Enhances Insulin Sensitivity in Minature Pigs", J. Nutr., pp. 1549-1553, (1996).

Belury, "Conjugated Dienoic Linoleate: A Polyunsaturated Fatty Acid with Unique Chemoprotective Properties", Nutrition Reviews, vol. 53, No. 4, pp. 83-89, (1995).

Bourre, et al., "The Effects of Dietary α-Linolenic Acid on the Composition of Nerve Membranes, Enzymatic Activity, Amplitude of Electrophysiological Parameters, Resistance to Poisons and Performance of Learning Tasks in Rats", J. Nutr., pp. 1880-1892, (1989).

Bourre, et al., "Dietary α-Linolenic Acid at 1.3 g/kg Maintains Maximal Docosahexaenoic Acid Concentration in Brain, Heart and Liver of Adult Rats", J. Nutr., pp. 1313-1319, (1993).

Broughton et al., "Frequency of (n-3) Polyunsaturated Fatty Acid Consumption Induces Alterations in Tissue Lipid Composition and Eicosanoid Synthesis in CD-1 Mice", J. Nutr., pp. 1104-1111, (1994).

Broughton, et al., "Reduced asthma symptoms with n-3 fatty acid ingestion are related to 5-series leukotriene production", Am. J. Clin. Nutr., pp. 1011-1017, (1997).

Carlson, Susan E., "Arachidonic Acid Status of Human Infants: Influence of Gestational Age at Birth and Diets with Very Long Chain n-3 and n-6 Fatty Acids", J. Nutr., pp. 1092S-1098S, (1996).

Carlson, et al., "Docosahexaenoic acid status of preterm infants at birth and following feeding with human milk or formula", Am. J. Clin. Nutr., 44, pp. 798-804, (1986).

Chalon et al., "Dietary Fish Oil Affects Monoaminergic Neurotransmission and Behavior in Rats", J. Nutr., pp. 2512-2519, (1998).

Clandinin, et al., "Docosahexaenoic Acid Increases Thyroid-stimulating Hormone Concentration in Male and Adrenal Corticotrophic Hormone Concentration in Female Weanling Rats", J. Nutr. 128, pp. 1257-1261, (1998).

Conquer, et al., "Supplementation with an Algae Source of Docosahexaenoic Acid Increases (n-3) Fatty Acid Status and Alters Selected Risk Factors for Heart Disease in Vegetarian Subjects", J. Nutr., pp. 3032-3039, (1996).

Cook, et al., "Immune Modulation by Altered Nutrient Metabolism: Nutritional Control of Immune-Induced Growth Depression", Poultry Science, 72, pp. 1301-1305, (1993).

Crawford, Michael A., "The Role of Dietary Fatty Acids in Biology: Their Place in the Evolution of the Human Brain", Nutrition Reviews, vol. 50, No. 4, pp. 3-11, (1992).

Crawford, Michael A., "The role of essential fatty acids in neural development: implications for perinatal nutrition", J. Clin. Nutr., 57(suppl.), pp. 703S-710S, (1993).

(56) References Cited

OTHER PUBLICATIONS

Crozier, Gayle L., "Medium-Chain Triglyceride Feeding over the Long Term: The Metabolic Fate of [14C]ctanoate and [14C]Oleate in Isolated Rat Hepatocytes", J. Nutr., pp. 297-304, (1988).

Drevon, Christian A., "Marine Oils and Their Effects", Nutrition Reviews, vol. 50, No. 4, pp. 38-45, (1992).

Endres, Stefan, "Messengers and mediators: interactions among lipids, eicosanoids, and cytokines", Am.J. Clin.Nutr., 57(suppl), 798S-800S, (1993).

Farrell, David J., "Enrichment of hen eggs with n-3 long-chain fatty acids and evaluation of enriched eggs in humans", Am. J. Clin. Nutr., 68, pp. 538-544, (1998).

Fernandez et al., "Fish consumption and cancer risk", American Journal of Clinical Nutrition, vol. 70, No. 1, pp. 85-90, (Jul. 1999).

Gabler et al., "Feeding long-chain n-3 polyunsaturated fatty acids during gestation increases intestinal glucose absorption potentially via the acute activation of AMPK," J Nutr Biochem, May 12, 2008 [Epub ahead of print] PMID: 18479897.

Frankel, et al., "The nutritional and metabolic impact of γ-linolenic acid (18:3ω6) on cats deprived of animal lipid", Br. J. Nutr., 39, pp. 227-231, (1978).

Garg, Abhimanyu, "High-monounsaturated-fat diets for patients with diabetes mellitus: a meta-analysis", Am J Clin Nutr, 67 (suppl), pp. 577S-582S, (1998).

Gerbi, et al., "Fish Oil Supplementation Prevents Diabetes-Induced Nerve Conduction Velocity and Neuroanatomical Changes in Rats", J. Nutr, pp. 207-213, (1998).

German et al., "Symposium: Biological Effects of Dietary Arachidonic Acid", J. Nutr., pp. 1076S-1080S, (1996).

Herbel, et el., "Safflower oil consumption does not increase plasma conjugated linoleic acid concentrations in humans", Am. J. Clin. Nutr., 67, pp. 332-337, (1998).

Hoffman, et al., "Effects of supplementation with ω3 long-chain polyunsaturated fatty acids on retinal and cortical development in premature infants", Am. J. Clin. Nutr., 57 (suppl), pp. 807S-812S, (1993).

Horrobin, David F., "Fatty acid metabolism in health and disease: the role of Δ-6-desaturase", Am. J. Clin. Nutr., 57(suppl), pp. 732S-737S, (1993).

Hulan, et al., "Omega-3 Fatty Acid Levels and Performance of Broiler Chickens Fed Redfish Meal or Redfish Oil", Cm J. Anim. Sci., 68, pp. 533-547, (1988).

Innis, Sheila M., "The colostrum-Deprived Piglet as a Model for Study of Infant Lipid Nutrition", J. Nutr., 123: 386-390, (1993).

Issfal, "International Society for the Study of Fatty Acids and Lipids Board Statement: Recommendations for the Essential Fatty Acid Requirement for Infant Formulas", Nutrition Today, vol. 30, No. 1, pp. 46, (1995).

Jensen, et al., "Lymphatic absorption of enterally fed structured triacylglycerol vs. physical mix in a canine model", Am. J. Clin. Nutr. 60, pp. 518-524, (1994).

Katan, M.B., "Fish and Heart Disease: What is the Real Story?", Nutrition Reviews, vol. 53, No. 8, pp. 228-230, (1995).

Kim et al., "Nutrition Chemoprevention of Gastrointestinal Cancers: A Critical Review", Nutrition Reviews, vol. 54 No. 9 pp. 759-279, (1996).

Kinsella, John E., "Food Lipids and Fatty Acids: Importance in food Quality, Nutrition, and Health", Food Technology, pp. 124-145, (1988).

Korver, et al., "Dietary Fish Oil or Lofrin, A 5-Lipoxygenase Inhibitor, Decrease the Growth-Suppressing Effects of Coccidiosis in Broiler Chicks", Poultry Science, 76, pp. 1355-1363, (1997).

Kretchmer, et al., "The role of nutrition in the development of normal cognition", Am. J. Clin. Nutr., 63, pp. 997S-1001S, (1996).

Luo, et al., "Dietary (n-3) Polyunsaturated Fatty Acids Improve Adipocyte Insulin Action and Glucose Metabolism in Insulin-Resistant Rats: Relation to Membrane Fatty Acids", J. Nutr., 126:, pp. 1951-1958, (1996).

MacDonald, et al., "Role of Linoleate as an Essential Fatty Acid for the Cat Independent of Arachidonate Synthesis", J. Nutr., 113: 1422-1433 (1983).

MacDonald, et al., "Effects of Linoleate and Arachidonate Deficiencies on Reproduction and Spermatogenesis in the Cat", J. Nutr., 114: 719-796, (1984).

Nair, et al., "Prevention of Cardiac Arrhythmia by Dietary (n-3) Polyunsaturated Fatty Acids and Their Mechanism of Action", J. Nutr., 127:383-393. (1997).

Neuninger, M., "Cerebral Cortex Docosahexaenoic Acid is Lower in Formula-Fed Than in Breast-Fed Infants", Nutrition Reviews, vol. 51, No. 8, pp. 238-241, (1993).

Odle, et al., "Utilization of Medium-Chain Triglycerides by Neonatal Piglets: Chain Length of Even-and Odd-Carbon Fatty Acids and Apparent Digestion/Absorption and Hepatic Metabolism", J. Nutr.., 121: 605-614 (1991).

O'Quinn, et al., "A comparison of modified tall oil and conjugated linoleic acid on growing-finishing pig growth performance and carcass characteristics", JAS-Midwestern Section ADSA ASAS. p. 61 (1998).

O'Shea, et al., "Conjugated linoleic acid in bovine milk fat: a food-based approach to cancer chemoprevention", Trends in Food Science & Technology., 9:192-196. (1998).

Pawlosky, et al., "Retinal and brain accretion of long-chain polyunsaturated fatty acids in developing felines: the effects of corn oil-based maternal diets". J. Clini. Nutr., 65: 465-472. (1997).

Reeves, et al., "AIN-93 Purified Diets for Laboratory Rodents: Final Report of the J. Nutr. Ad Hoc Writing Committee on the Reformulation of the AIN-76A Rodent Diet" J. Nutr., 123: 1939-1951 (1993).

Sanders, et al., "A comparison of the influence of breast-feeding and bottle-feeding on the fatty acid comnosition of the erythrocytes". Br. J. Nutrition, 41, pp. 619-623. (1979).

Simpoulos, Artemis P., "Omega-3 fatty acids in health and disease and in growth and development", Am. J. Clin. Nutr., 54, pp. 438-463. (1991).

Turek, et al., "Dietary Polyunsaturated Fatty Acids Modulate Responses of Pigs to Mycoplasma hyopneumoniae infection", J. Nutr., 126: 1541-1548 (1996).

Wallingford, et al., "Development of the Health Claims Regulations: The Case of Omega-3 Fatty Acids and Heart Disease", Nutrition Reviews, vol. 49, No. 11, pp. 323-331, (1991).

Wanasundara, et al., "Positional Distribution of Fatty Acids in Triacylglycerols of Seal Blubber Oil", Journal of Food Lipids, 4, pp. 51-64, (1997).

Wander, et al., "The Ratio of Dietary (n-6) to (n-3) Fatty Acids Influences Immune System Function, Eicosanoid Metabolism, Lipid Peroxidation and Vitamin E Status in Aged Dogs", J. Nutr., 127: 1198-1205, (1997).

Watts, et al., "Dietary fatty acids and progression of coronary artery disease in men", Am. J. Clin. Nutr., 64: 202-209, (1996).

Whelan, Jay, "Antagonistic Effects of Dietary Arachidonic Acid and n-3 Polyunsaturated Fatty Acids", J. Nutr., 126: 1086S-1091S, (1996).

Whelan, Jay, "Polyunsaturated Fatty Acids: Signaling Agents for Intestinal Cancer?", Nutrition Today, vol. 32, No. 5, pp. 213-218, (1997).

Wu, et al., "Immunologic effects of marine- and plant-derived n-3 polyunsaturated fatty acids in nonhuman primates" Am. J. Clin. Nutr., 63: 273-280, (1996).

Yeh, et al., "Enrichment of (n-3) Fatty Acids of Suckling Rats by Maternal Dietary Menhaden Oil", J. Nutr., 120: 436-443 (1990).

Yonekubo, et al., "Dietary Fish Oil Alters Rat Milk Composition and Liver and Brain Fatty Acid Composition of Fetal and Neonatal Rats". J. Nutr., 123: 1703-1708. (1993).

Zemel, Michael B., "Insulin Resistance, Obesity and Hypertension: Insulin Overview", J. Nutr., 125: 1715S-1717S, (1995).

Blesbois, et al., "Effect of Dietary Fat on the Fatty Acid Composition and Fertilizing Ability of Fowl Semen", Biology of Reproduction, 56, pp. 1216-1220, (1997).

Trujillo, et al., "Ingestion of n-3 polyunsaturated fatty acids and ovulation in rats", Journal of Reproduction and Fertility, 105 pp. 197-203, (1995).

(56) References Cited

OTHER PUBLICATIONS

Ringo, et al., "The effect of dietary fatty acids on lactic acid bacteria associated with the epithelial mucosa and from faecalia of Arctic charr, *Salvelinus alpinus* (L)", Journal of Applied Microbiology, 85, pp. 855-864, (1998).

Schingoethe, et al., "Lactational Responses of Dairy Cows Fed Unsaturated Fat from Extruded Soybeans or Sunflower Seeds". J. Dairy Sci. 79, pp. 1244-1249, (1996).

Ackerman, Lowell, "Dermatologic uses of fatty acids in dogs and cats", Veterinary Medicine, pp. 1149-1155, (1995).

Aydin, et al., "Dietary Conjugated Linoleic Acid Inhibits the Hatchability of Pigeon Eggs", SPSS Abstracts, S81 pp. 115 (1999).

Aydin, et al., "Olive Oil Alleviated the Adverse Effects of Dietary Conjugated Linoleic Acid on Hatchability", SPSS Abstracts, S82, pp. 115 (1999).

Aydin, et al., "Addition of Olive Oil Prevents Pink Discoloration of Egg white by Dietary Conjugated Linoleic Acid", SPSS Abstracts, S83, p. 115 (1999).

Banni, et al., "Conjugated Linoleic Acid and Oxidative Stress", JAOCS, vol. 75, No. 2, pp. 261-267, (1998).

Bauer, John F., "Management of Spontaneous Canine Renal Disease by Dietary Polyunsaturated Fatty Acids". Proc. 13th ACVIM Forum, pp. 477-479. (1995).

Bauer, John E., "New Concepts of Polyunsaturated Fatty Acids in Dog and Cat Diets", Veterinary Clinical Nutrition vol. 4 No. 1, pp. 29-33, (1997).

Bauer, et al., "Effect of Diet and Fatty Acid Supplementation on Lipids and Lipoproteins in Canine Renal Disease", Proc. 12th ACVIM Forum, 52 pp. 986, (1994).

Berry, Elliot M., "Dietary fatty acids in the management of diabetes mellitus", Am. J. Clin. Nutr., 66 (suppl), pp. 991S-997S, (1997).

Billman, et al., "Prevention of Ischemia-Induced Cardiac Sudden Death by n-3 Polyunsaturated Fatty Acids in Dogs", Lipids, vol. 32, No. 11, pp. 1161-1168, (1997).

Boothe, Dawn M., "Medical Management of Osteoarthrits", Proc. 14th ACVIM Forum, pp. 274-277, (1996).

Boudreaux, et al., "The Effects of Varying Dietary n-6 to n-3 Fatty Acid Ratios on Platelet Reactivity, Coagulation Screening Assays, and Antithrombin III Activity in Dogs", Journal of the American Animal Hospital Association, 33 pp. 235-243, (1997).

Bourre, et al., "Alterations in the Fatty Acid Composition of Rat Brain Cells (Neurons, Astrocytes, and Oligodendrocytes) and of Subcellular Fractions (Myelin and Synaptosomes) Induced by a Diet Devoid of n-3 Fatty Acids", Journal of Neurochemistry, 43, pp. 342-348, (1984).

Brown, Scott A., "Dietary Fatty Acid Supplementation and Chronic Renal Disease", Proc. 13th ACVIM Forum, pp. 470-472, (1995).

Brown, et al., "Dietary Fatty Acid Composition Affects Renal Function in Cats", Proc. 16th ACVIM Forum, 104, pp. 713 (1998).

Campbell, Karen L., "Fatty Acid Supplementation and Skin Disease", Adv. in Clinical Dermatol., vol. 20, No. 6. pp. 1475-1486. (1990).

Campbell, et al., "Effects of Four Diets on Serum and Cutaneous Fatty Acids, Transepidermal Water Losses, Skin Surface Lipids, Hydration and Condition of the Skin and Haircoat of Dogs", 11th Proceedings of AAVD/ACVD meeting, pp. 80-81, (1995).

Chin, et al., "Dietary Sources of Conjugated Dienoic Isomers of Linoleic Acids, a Newly Recognized Class of Anticarcinogens", Journal of Food Composition and Analvsis, 5, pp. 185-197, (1992).

Connor, et al., "Arc fish oils beneficial in the prevention and treatment of coronary artery disease?", Am. J. Clin. Nutr., 66(suppl), pp. 1020S-1031S, (1997).

Connor, et al., "Essential Fatty Acids: The Importance of n-3 Fatty Acids in the Retina and Brain", Nutrition Reviews, vol. 50, No. 4, pp. 21-29, (1997).

Down, et al., "Dyslipoproteinemia of Chronic Renal Failure: Its Relevance to Canine Progressive Kidney Disease". Compendium, 18, pp. 65-74, (1996).

Dugan, et al., "The effect of conjugated linoleic acid on fat to lean repartitioning and feed conversion in pigs", Canadian Journal of Animal Science 77, pp. 723-775 (1997).

Emken, et al., "Effect of Dietary Arachidonic Acid on Metabolism of Deuterated Linoleic Acid by Adult Male Subjects", Lipids, vol. 33, No. 5, pp. 471-480, (1998).

Freese, et al., "α-linolenic acid and marine long-chain n-3 fatty acids differ only slightly in their effects on hemostatic factors in healthy subjects", Am J. Clin Nutr., 66 pp. 591-598 (1997).

Goodwin, John-Karl, "The Nondrug Therapy of Heart Disease in the Dog and Cat", Emerging Science & Technology. pp. 24-29, (1996).

Goodwin, et al., "The role of dietary modification and nondrug therapy in dogs and cats with congestive heart failure", Veterinary Medicine, pp. 919-926, (1998).

Goodwin, et al., "Role of Lipoxygenase Metabolites of Arachidonic Acid in T Cell Activation", Annals New York Academy of Sciences 574:201-207, (1988).

Grauer, et al., "Effects of dietary n-3 fatty acid supplementation versus thromboxane synthetase inhibition on gentamicin-induced nephrotoxicosis in healthy male dogs", ωJVR, vol. 57, No. 6, pp. 948-956. (1996).

Grimsgaard, et al., "Highly purified eicosapentaenoic acid and docosahexaenoic acid in humans have similar triacylglycerol-lowering effects but divergent effects on serum fatty acids", Am. J. Clin. Nutr., 66, pp. 649-659, (1997).

Guilford, W.G., "New ideas for the dietary management of gastrointestinal tract disease", Journal of Small Animal Practice 35, pp. 620-624, (1994).

Hall, Jean A., "Potential Adverse Effects of Long-Term Consumption of (n-3) Fatty Acids", The Compendium, vol. 18, No. 8, pp. 879-895, (1996).

Hall, et al., "Effect of dietary n-6 to n-3 fatty acid ratio on complete blood and total white blood cell counts, and T-cell subpopulations in aged dogs", AJVR, vol. 60, No. 3, pp. 319-327, (1999).

Hansen, et al., "Duration of effects of dietary fish oil supplementation on serum eicosapentaenoic acid and docosahexaenoic acid concentrations in dogs", AJVR, vol. 59, No. 7, pp. 864-868, (1998).

Harris, et al., "Influence of n-3 fatty acid supplementation on the endogenous activities of plasma lipases", Am. Clin. Nutr., 66, pp. 254-260, (1997).

Hashim, et al., "Medium Chain Triglyceride in Early Life: Effects on Growth of Adipose Tissue", Lipids, vol. 22, No. 6, pp. 429-434, (1987).

Holub, Bruce J., "The Role of Omega-3 Fatty Acids in Health and Disease", Proc. 13th ACVIM Forum, pp. 452-455, (1995).

Hwang, et al., "Does vegetable oil attenuate the beneficial effects of fish oil in reducing risk factors for cardiovascular disease?", Am. J. Clin. Nutr., 66. pp. 89-96, (1997).

Ikeda, et al., "Effects of Long-Term Feeding of Marine Oils with Different Positional Distribution of Eicosapentaenoic and Docosahexaenoic Acids on Lipid Metabolism, Eicosanoid Production, and Platelet Aggregation in Hypercholesterolemic Rats", Lipids, vol. 33, No. 9, pp. 897-904, (1998).

Ip, "Review of the effects of trans fatty acids, oleic acid, n-3 polyunsaaturated fatty acids, and conjugatted linoleic acid on mammary carcinogenesis in animals". Am. J. Clin. Nutr., 66 (suppl), pp. 1523S-1529S, (1997).

Jenski, et al., "The Triggering Signal Dictates the Effect of Docosahexaenoic Acid on Lymphocyte Function in vitro" Lipids vol. 33, No. 9, pp. 869-878, (1998).

Johnston, John M., "Gastrointestinal Tissue", In: Lipid Metabolism of Mammals, vol. 1, Plenum, pp. 151-187, (1977).

Kay, Marguerite M.B., "An Overview of Immune Aging", Mechanisms of Ageing and Development, 9, pp. 39-59 (1979).

Leaf, et al., "Cardiovascular Effects on n-3 Fatty Acids", The New England Journal of Medicine, vol. 318, No. 9. pp. 549-557, (1988).

MacDonald, et al., "Essential fatty acid requirements of cats: Pathology of essential fatty acid deficiency", Am. J. Vet. Res. vol. 45, No. 7, pp. 1310-1317, (1984).

Meyer, H., "Nutrient Digestibility and Its Relationship to Alimentary Disorders in Dogs", Pergamon Press, pp. 55-69, (1984).

(56) References Cited

OTHER PUBLICATIONS

Miller, et al., "Feeding Conjugated Linoleic Acid to Animals Partially Overcomes Catabolic Reponses Due to Endotoxin Injection", Biochemical and Biophysical Research Communications, 198, pp. 1107-1112, (1994).

Miller, et al., "Influence of Feeding Conjugated Linoleic Acid on Body Composition in Healthy Adult Cats", Proc. 17th ACVIM, 150, pp. 729, (1999).

Miller et al., "Treatment of Dogs With Hip Arthritis With a Fatty Acid Supplement", Canine Practice, vol. 17, No. 6, pp. 6-8, (1992).

Mooney, et al., "Evaluation of the effects of omega-3 fatty acid-containing diets on the inflammatory stage of wound healing in dogs", AJVR, vol. 59, No. 7, pp. 859-863, (1998).

Moore, et al., "Effect of Dietary Alpha-Linolenic Acid on Responses of Horses to Endotoxin", Veterinary Clinical Nutrition, vol. 3, No. 1, pp. 16-18, (1996).

Newton, Ian S., "Long Chain Fatty Acids in Health and Nutrition", Journal of Food Lipids, 3, pp. 233-249, (1996).

Ogilvie, Gregory, "Nutritional Anticancer Therapy: Frontiers for Cure!", 62nd Annual AAHA Meeting Proc., pp. 66-69. (1995).

Ogillvie, Gregory, "Recent Discoveries: Nutrition and Cancer—Are Eicosanoids the Answer?", Veterinary Clinical Nutrition. vol. 3. No. 3, pp. 78-82. (1996).

Ogilvie, et al., "Nutrition and Cancer", Veterinary Clinics of North America: Small Animal Practice, vol. 20, No. 4, pp. 969-985, (1990).

Peterson, et al., "Eicosapentaenoic and Docosahexaenoic Acids Alter Rat Spleen Leukocyte Fatty Acid Composition and Prostaglandin E2 Production But Have Different Effects on Lymphocyte Functions and Cell-Mediated Immunity", Lipids, vol. 33, No. 2, pp. 171-180, (1998).

Peitinen, et al., "The Role of Nutrition in the Prevention and Treatment of Hypertension", Advances in Nutritional Research, vol. 8, pp. 35-73. (1990).

Plotnick, A. N., "The role of omega-3 fatty acids in renal disorders", JAVMA, vol. 209, No. 5, pp. 906-910, (1996).

Raz, et al., "Dietary Fish Oil Inhibits ω-Desaturase activity in vivo", JAOCS, vol. 75, No. 2, pp. 241-245, (1998).

Reinhart, Gregory A., "Review of Omega-3 Fatty Acids and Dietary Influences on Tissue Concentrations", Proc. Iams International Symposium, pp. 235-242, (1996).

Ross, Linda A., "Controversies in the Mangement of Chronic Renal Failure", Proc. 14th ACVIM Forum, pp. (1996), 798-799.

Rush, John E., "Alternative Therapies for Heart Failure Patients", Proc. 14th ACVIM Forum, pp. 151-153, (1996).

Sehedio, et al., "Metabolites of conjugated isomers of linoleic acid (CLA) in the rat", Biochimica et Bionhvsica Acta. 1345, pp. 5-10, (1997).

Johanson, et al., "Within 13 days lipid source alters bone accretion and minneral balance in neonatal pigs", J. Anim Sci., vol. 76, Suppl. 1, 683 pp. 176, (1998).

Sinclair, A. J., "Metabolism of Linoleic Acid in the Cat", Lipids, 14, pp. 932-936, (1979).

Thiel, et al., "Conjugated linoleic acid improves performance and body composition in swine", ASAS Midwest Meeting Abstracts. 127, pp. 61, (1998).

Van den Berg, et al., "Reinvestigation of the Antioxidant Properties of Conjugated Linoleic Acid", Lipids, vol. 30, No. 7 pp. 599-605, (1995).

Vaughn, et al., "Evaluation of Dietary N-6 to N-3 Fatty Acid Ratios on Leukotriene B Synthesis in Dog Skin and Neutrophils", J. Vet. Int. Med., 49, pp. 155, (1994).

Waldron, et al., "Role of long-chain polyunsaturated n-3 fatty acids in the development of the nervous system of dogs and cats", JAVMA, vol. 213, No. 5, pp. 619-622, (1998).

Waldron, et al, "Canine Neutrophil Phagocytosis is Correlated with membrane Fluidity", Proc. 17th ACVIM, 144, pp. 728, (1999).

Waldron, et al., "18 and 20 Carbon N-3 Fatty Acids Differentially Affect Canine Neurtophil Function At the Same N-6/N-3 Ratio", Proc. 17th ACVIM, 145, pp. 728, (1999).

White, P. D., "Essential Fatty Acids: Use in Management of Canine Atopy", Compendium, pp. 451-457, (1993).

Zhang, et al., "Oxidative Stability of Conjugated Linoleic Acids Relative to Other Polyunsaturated Fatty Acids" JAOCS, vol. 74, No. 12, pp. 1611-1613, (1997).

Badart-Smook, et al., "Fetal growth is associated positively with maternal intake of riboflavin and negatively with maternal intake of linoleic acid", J. Am. Diet. Assoc., 97. pp. 867-870, (1997).

Bauer, et al., "Dietary n-6 fatty acid supplementation improves ultrafiltration in spontaneous canine chronic renal failure", ACVIM abstracts, p. 126, (1994).

Bauer, et al., "Dietary flaxseed in dogs results in differential plasma transport and metabolism of n-3 polyunsaturated fatty acid species" Proc. Waltham Symposium, p. 34, (1997).

Campbell, K. L., "Fatty acids in dermatology: Choices in treatment", Proc. Central Veterinary Conference, pp. 386-389, (1999).

Doyle, E., "Scientific forum explores CLA knowledge", Inform, 9: 69-73, (1998).

Dunshea, et al., "Dietary conjugated linoleic acid decreases back fat in finisher gilts", J. Anim. Sci., 76 (Suppl, 1):131: 723-735, (1998).

Fernandes, G., "Dietary lipids and risk of autoimmune disease", Clin. Immunol. Immunopathol., 72: 193-197, (1994).

Olsen, et al., "Intake of Marine Fat, Rich in (n-3) Polyunsaturated Fatty Acids, May Increase Birthweight by Prolonging Gestation", The Lancet, pp. 367-369. (1986).

Innis, S.M., "Essential dietary lipids.", In: E.E. Ziegler and L. J. Filer (Ed), Present Knowledge in Nutrition, 71 Ed. ELSI Press, pp. 58-66, (1996).

Jiang, et al., "Production of conjugated linoleic acid by dairy starter cultures", J. Appl. Micro., 85: 95-102, (1998).

Jumpsen, et al., "Small changes of dietary (n-6) and (n-3) fatty acid content ratio alter phosphatidyl ethanolamine and phosphatidyl choline fatty acid composition during development of neuronal and glial cells in rats", J. Nutr., 127, pp. 724-731, (1997).

Kinsella, J. E., "α-Linolenic acid: Functions and effects on linoleic acid metabolism and eicosanoid-mediated reactions", Adv. Food and Nutr. Res. 35, pp. 1-184, (1991).

Lloyd, D. H., "Dietary supplementation and the skin", Proc. World Sm. Animal Vet. Assn., pp. 74-76, (1991).

Logas, D., "Double blind crossover study with high-dose eicosapentaenoic acid supplementation for the tretment of canine allergic pruritis", Proc. Ann. Meeting Am. Acad. Vet. Dermatol/Am. Coll. Vet. Derm., 9:37, (1993).

McLean, et al., Factors determining the essential fatty acid requirements of the cat, in: Burger, I.H. and J. P. W. Rivers, (ed.), Nutrition of the dog and cat, Waltham Symposium No. 7, pp. 329-342, (1989).

Mercuri, et al., "Depression in microsomal desaaturation of linoleic to gamma linolenic acid in the alloxan diabetic rat" Biochim. Biophys. Acta. 116, pp. 407-411, (1966).

Miller, W. H., Jr., "Fatty acid supplements as anti-inflammatory agents", In R. W. Kirk (Ed.), Current Veterinary Therapy, pp. 563-565, (1989).

Ogilvie, G. K., Enteral and parenteral therapy for the cancer patient, Proc. World Sm. An. Vet. Assn. 16th World Congress, pp. 267-270, (1991).

Osada, et al., "Dietary oxidized cholesterol modulates cholesterol metabolism and linoleic acid desaturation in rats fed highcholesterol diets", Lipids, 31 pp. 757-764 (1998).

Saker, et al., "Manipulation of dietary omega-3 and omega-6 fatty acids alters plalet function in cats", Proc. Waltham International Symposium p. 36, (1997).

Spurlock et al., "Environment, disease impact on performance reviewed", Feedstuffs, 69(44), pp. 13-15, 17-19, (1997).

Toft, et al., "Effects on n-3 polyunsaturated fatty acids on glucose homeostasis and blood pressure in essential hypertension". Ann. Intern. Med., 123, pp. 911-918 (1995).

Turek, et al., "Modulation of macrophage cytokine production by conjugatged linoleic acids is influenced by the dietary n-6; n-3 fatty acid ratio", Nutri. Biochem., 9: 258-266, (1998).

Vilaseca et al., "Dietary fish oil reduces progression of chronic inflammatory lesions in a rat model of grannulomatous colitis", Gut. 31: 539-544, (1990).

(56) References Cited

OTHER PUBLICATIONS

White, P. D., "Effects of gamma linolenic acid supplementation on serum and cutaneous fatty acid profiles and cutaneous eiosanoids in normal and atopic dogs", A double-blind, placebo controlled crossover study, Proc. 2nd World Congr. Vet. Derm., 2: 32-33, (1992).

Yurawecz, et al., :A new conjugated linoleic acid isomer, 7 trans, 9 cisoctadecadlenoic acid, in cow milk, cheese, beef and human milk and adinose tissue, (1998).

Abayasekara, et al., "Effects of Altering Dietary Fatty Acid composition on Prostaglaandin Synthesis and Fertility", Prostaglandins, Leukotrienes and Essential Fatty Acids. vol. 61(5), pp. 275-287, (1999).

Quackenbush, et al., "The Effectiveness of Linoleic, Arachidonic, and Linolenic Acids in Reproduction and Lactation", Jour. of Nutrition. vol. 2, pp. 213-224, (1942).

Annales Universitatis Mariae Curie-Sklodowska, Sectio Ee Zootechnica, vol. 13, 1995, pp. 71-76.

R. Cordoba et al., "The effect of feeding salmon oil during pregnancy on causes of piglet deaths prior to weaning" Proceeds of the British Society of Animal Science, 2000, p. 105.

Database Biosis 'Online!, Biosciences Information Services, Philadelphia, PA, US; 1991, Migdal W. et al.: "Effect of Fish Oil in the Diets for Sows on Chemical Compositions of Milk and Results of Piglets Management" Database accession No. PREV199192095383 & ACTA Agraria Et Silvestria Series Zootechnia, vol. 29, 1991, pp. 47-58.

I.M. Bland et al.: "The effects of neonatal piglet behaviour and tissue composition of feeding sows a diet containing a high level of docosahexaenoic acid (DHA) in late gestation and lactation", Proceedings of the British Society of Animal Science, 1997, p. 111.

Deng-Qun, Shu, Jiangxi Journal of Animal Husbandry & Veterinary, vol. 2, pp. 1-13, Relations Between Fat and the Physiological Biochemistry of Livestock and Fowl (1994).

Yoshii et al., *Journal of Inclusion Phenomena and Molecular Recognition in Chemistry*, 1996; 217-220.

Wikipedia entry for "prill", accessed May 21, 2008.

Rooke et al., Animal Science, 2001, 73: 489-500.

"Mojonnier Method," A.O.A.C. 954.02, 15th Edition, 1990 (book reference available upon equest).

NCR, Nutritional Requirements of Swine, 10th ed., Washington, D.C.: Nat'l. Acad. Press (1998).

NCR Poultry Requirements, National Research Council, 1994, Nutrient Requirements of Poultry, 9th ed., NRC, Washington, DC.

Vicario, "Dietary Unsaturated Long-Chain Fatty Acid Modify D-Glucose Absorption in Weaning Rats," *JPGN*, 2005; 40:151-156.

Suchankova, "Dietary polyunsaturated fatty acids enhance hepatic AMP-activated protein kinase activity in rats." *Biochemical and Biophysical Research Communications*, 2005. 376:851-858.

Meluzzi et al., "Effects of Dietary Vitamin E on the Quality of Table Eggs Enriched with n-3 Long-Chain Fatty Acids." *Poultry Science*. 79: 539-545 (2000).

Lucy, "The Science behind Improving Reproduction in Postpartum Dairy Cows with Essential Fatty Acids," Presented at the Southwest Nutrition Conference—Arm & Hammer Pre-Symposium, Pheonix, Arizona, Feb. 20, 2003.

Baucells et al., "Incorporation of Different Polyunsaturated Fatty Acids into Eggs," *Poultry Science*, 79: 51-59 (2000).

Gatlin et al., "The Effects of Dietary Fat Sources, Levels, and Feeding Intervals on Pork Fatty Acid Comnosition " *J. Anim. Sci.* 80: 1006-1615 (2007).

Howe et al., "Tuna Fishmeal as a Source of DHA for n-3 PUFA enrichment of Pork, Chicken, and Eggs (Abstract)." *Lipids*. 37(11): 1067-76 (2002).

Hooge, "Marine Algae as Dietary Source of Omega-3 Fatty Acids (DHA) (Abstract)," *Scientific Reviews*, Aug. 28, 2001 (available at FEEDinfo.com).

Mariott et al., "Characteristics of Pork with Docosahexaenoic Acid Supplemented in the Diet (Abstract)," *Journal of Muscle Foods*, 13(4): 253-263 (2002).

Ashes et al., "Incorporation of n-3 Fatty Acids of Fish Oil into Tissue and Serum Lipids of Ruminants," *Lipids*, 27(8): 629-631 (1992).

Bassaganya-Riera et al., "Arachidonic Acid- and Docosahexaenoic Acid-Enriched Formulas Modulate Antigen-Specific T-cell Responses to Influenza Virus in Neonatal Piglets," *Am. J. Clin. Nutr.*, 85: 824-836 (2007).

O'Conner et al., "The Effect of Dietary Fish Oil Supplementation on Exercising Horses," *J. Amer. Sci.*, 82: 2978-2984 (2004).

Herber et al., "Dietary Marine Algae Promotes Efficient Deposition for n-3 fatty acids for the production of enriched shell eggs (Abstract)." *Poultry Science*. 75(12): 1501-1507 (1996).

Herber-McNeill et al., "Dietary Marine Algae Maintains Egg Consumer Acceptability While Enhancing Yolk Color." *Poultry Science*. 77: 493-496 (1998).

Heinemann et al., "Docosahexaenoic Acid and Neurological Development in Animals," *Vet Med Today: Timely Tonics in Nutrition*, 228(5): 700-705 (2006).

Burke et al., "Effect of Ruminant Grade Menhaden Fish Meal on Reproductive and Productive Performance o Lactating Dairy Cows." *J. Dairy Sci.*, 80: 3386-3398 (1997).

Surai et al., "Effect of Long-Term Supplementation With Arachidonic or Docosahexaenoic Acids on Sperm Production in the Broiler Chicken." *J. of Reproduction and Fertility*, 120: 257-264 (2000).

Korver et al., "Effect of Dietary Energy Level and Oil Source on Broiler Performance and Response to an Inflammatory Challenge," *Poultry Science*, 77: 1217-1227 (1998).

Korver et al., "Dietary Fish Oil Alters Specific and Inflammatory Immune responses in Chicks," *J. Nutr.*, 127: 2039-2046 (1997).

Van Elswyk, "Comparison of n-3 Fatty Acid Sources in Laying Hen Rations for Truprovement of Whole Egg Nutritional Quality: A Review (Abstract)," *Br. J. Nutrition*, 78(Suppl 1): S61-9 (1997).

Zaniboni et al., "Combined Effect of DHA and Alpha-Tocopherol Enrichment on Sperm Quality and Fertility in the Turkey (Abstract)." *Theriogenology*. 65(9): 1813-27 (2006).

Hansen et al., "Effects of Dietary Flaxseed Oil Supplementation on Equine Plasma Fatty Acid Concentrations and Whole Blood Platelet Aggregation (Abstract)," *J. Vet. Intern. Med.*, 16(4): 457-63 (2002).

McCann et al., "Effect of Intravenous Infusion of Omega-3 and Omega-6 Lipid Emulsions on Equine Monicyte Fatty Acid Composition and Inflammatory Mediator Production In Vitro (Abstract)," *Shock.*, 14(2): 222-8 (2000).

Korniewicz et al., "Effect of Dietary Fish Oil on Fattening Performance of Pigs," *Ann. Anim. Sci.*, 2(1): 159-170 (2002).

Strzezek et al., "Effects of Dietary Supplementation with Polyunsaturated Fatty Acids and Antioxidants on Biochemical Characteristics of Boar Semen." *Reproductive Biology*, 4(3):271-287 (2004).

Ambrose et al., "Dietary Fatty Acids and Dairy Cow Fertility," *Advances in Dairy Technology*, 15: 35-47 (2003).

Kelso et al., "The Effects of Dietary Supplementation With Docosahexaenoic Acid on the Phospholipid Fatty Acid Composition of Avian Spermatozoa," *Comp. Biochem. Physiol.*, 118B(1): 65-69 (1997).

Surai et al., "Lipid Peroxidation in Avian Semen: Protective Effect of Seminal Plasma," *British Poultry Science*, 39(5): 57-58 (1998).

Ajuyah et al., "The Effect of Maternal Dietary Omega-3 Fatty Acids on Hatchability and Growth of Broiler Chickens" *Proc. Aust. Poult. Sci. Sym*. 15: 154-158 (2003).

O'Conner et al., "Dietary Fish Oil Supplementation Affects Serum Fatty Acid Concentrations in Horses," *J. of Animal Science.*, published online May 15, 2007.

Pike, "Fish Products for Animal Health: The Role of Long Chain Omega-3 Fatty Acids," *Feedstuffs*, 72(50): 11-13, 16 (2000).

Friesen, "Maternal Dietary Fat Alters Amniotic Fluid and Fetal Intestinal Membrane Essential n-6 and n-3 Fatty Acids in the Rat." *Am. J. Physiol. Gastrointest. Liver Physiol.*, 290:G505-g510 (2006).

Gabler, et al., "In Utero and Postnatal Exposure to Long Chain (n-3) PUFA Enhances Intestinal Glucose Absorntion and Eneruv Stores in Weanling Pigs", *The Journal of Nutrition*. 137: 2151-2358 (2007).

Jarocka-Cyrta et al., "Early dietary experience influences ontogeny of intestine in response to dietary lipid chanties in later life", *Am. J. Physiol Gastrointest Liver Physiol* 275:250-258, 1998.

(56) References Cited

OTHER PUBLICATIONS

Lopez-Pedrosa et al., "Severe Malnutrition Alters Lipid Composition and Fatty Acid Profile of Small Intestine in Newborn Piglets", *J. Nutrition*, 128: 224-933, 1998.

Lopez-Pedrosa et al., "Dietary Phospholipids Rich in Long-Chain Polyunsaturated Fatty Acids Improve the Repair of Small Intestine in Previously Malnourished Piglets", *J. Nutrition*, 129: 1149-1155, 1999.

Thomson et al., "Evidence for critical-period programming of intestinal transport function: variations in the dietary ratio of polyunsaturated to saturated fatty acids alters ontogeny of the rat intestine", *Biochimica et Biophysica Acta*, 1001, 302-315, 1989.

Spencer et al., "Diet modifications to improve finishing pig growth performance and pork quality attributes ditrinp neriods of heat stress," *Journal of Animal Science*, 2005 83. 243-254.

Erickson HH et al., "Exercise-induced pulmonary hemorrhage: current concepts," In: Lekeux, P, ed. *Equine Respiratory Diseases*, 2007, B0320.1107.

Erickson HH et al., "Novel and emerging therapies for EIPH," *Proc ACVIM*, 2004; 22:734-736.

Hinchcliff KW et al., "Association between exercise-induced pulmonary hemorrhage and performance in Thoroughbred racehorses." *J Am Vet Med Assoc.*, 2005: 227:768-774.

Art T et al., "Effect of exercise on the partitioning of equine respiratory resistance," *Equine Vet J*, 1988; 20:268-273.

Holcombe S.J. et al., "Effect of commercially available nasal strips on airway resistance in exercising horses." *Am J Vet Res*. 2002: 63:1101-1105.

Erickson H.H., "A review of exercise-induced pulmonary hemorrhage and new concepts for prevention," *AAEP Proc*. 2000; 46:193-196.

Poole Dc et al., "Effects of external nasal support on pulmonary gas exchange and EIPH in the horse," *J Equine Vet Sci*, 2000; 20:578-585.

Kindig CA et al., "Efficacy of nasal strip and furosemide in mitigating EIPH in Thoroughbred horses," *J Appl Physiol*, 2001; 91:1396-1400.

Geor RJ et al., "Effects of an external nasal strip and frusemide on pulmonary haemorrhage in Thoroughbreds following high-intensity exercise," *Equine Vet J*, 2001; 33:577-584.

Valdez SC et al., "Effect of an external nasal dilator strip on cytologic characteristics of bronchoalveolar lavaee fluid in Thoroughbred racehorses." *J Am Vet Med Assoc*. 2004; 224:558-561.

McDonough P et al., "Effect of furosemide and the equine nasal strip on exercise-induced pulmonary haemorrhage and time-to-fatigue in maximally exercising horses," *Equine Comp Ever Physiol*, 2004; 1:177-184.

McKane SA et al., "Equine bronchoalveolar cytology: survey of Thoroughbred racehorses in training," *Aust Vet J*. 1993; 70:401-404.

Newton Jr et al., "Evidence of an association between inflammatory airway disease and EIPH in young Thoroughbreds during training." *Equine Vet J. Suppl*. 2002: 34:417-424.

Mills PC et al., "Nitric oxide during exercise and pulmonary disease in the horse," *Pferdeheikunde*, 1996; 12:551-556.

Mills PC et al., "Nitric oxide and exercise in the horse," *J Physiol (London)*, 1996; 495:863-874.

Kindig CA et al., "NO inhalation reduces pulmonary artery pressure but not hemorrhage in maximally exercising horses," *J Appl Physiol*, 2001; 91:2674-2678.

Epp TS et al., "The effect of herbal supplementation on the severity of exercise-induced pulmonary haemorrhage," *Equine Comp Exer Physiol*, 2005; 2:17-25.

Portier K et al., "The effects of dietary N-3 and antioxidant supplementation on erythrocyte membrane fatty acid composition and fluidity in exercising horses," *Equine Vet J Suppl.*, 2006: 36:279-284.

Bayly WM et al., "Effects of furosemide on exercise-induced alterations in haemostasis in Thoroughbred horses exhibiting post-exercise epistaxis," In Snow DH et al., eds., *Equine Exercise Physiology*, Cambridge, Granta Editions, 1983; 64-70.

Johnstone IB et al., "Hemostatic studies in racing Standardbred horses with exercise-induced pulmonary hemorrhage. Hemostatic parameters at rest and after moderate exercise." *Can J Vet Res*. 1991: 55:101-106.

I Ieidmann P et al., "Laboratory measures of hemostasis and fibrinolysis after intravenous administration of aminocaproic acid in clinically normal horses and ponies." *Am J Vet Res*. 2005. 66:313-318.

Leskanich et al., *British Journal of Nutrition*, 1999, 81(2): 87-106.

Sun et al., *Dalian Shuichan Xueyuan Xuebao*, 2004, 19(2): 146-149.

I Ienderson et al., "Leukotriene Production and Inactivation by Normal, Chronic Granulomatous disease and Mveloperoxidase-deficient Neutrophils", 1983. 258(22). 13522-13527.

Anonymous, "Add OOMPH with Omegas," Equinews [online], 2006, 9(4): 10-11, Retrieved online at URL: http://www.ker.com/library/Equinews/v9n4/v9n410.pdf> [retrieved Mar. 25, 2013].

Anonymous, "EO.3—Benefit through balance," KERx, Feb. 16, 2007, Retrieved online at URL: http://www.kerx.com/products/EO3/info.html [retrieved Mar. 25 2013].

Marlin et al., Proceedings of a Havemeyer Workshop on Exercise-Induced Pulmonary Hemorrhage, Havemever Foundation Monograph. Mar. 9. 2006. 20: 1-28.

Pike, IFOMA: Technical Bulletin No. 28, May 1999.

Irie et al., J. Anim. Science, 1992, 70: 470-477.

"Docosahcxaenoic acid", Jul. 15, 2014, Retrieved from: URL:http://en.wikipedia.org/w/index.php?title=Special:Book&bookcmd=download&collection_id=b9aabf2a49bdd3af&writer=rl& return_to=Docosahexacid.

Anonymous: "cis-5,8,11,14,17-Eicosapentaenoic acid analytical standard: Sigma Aldrich", Jul. 15, 2014, Retrieved from: URL: http://www.sigmaaldrich.com/catalog/product/fluka/44864?lang=de ion=DE.

Archer et al., "Effect of dietary fish oil on lung lipid profile and hypoxic pulmonary hypertension", 1989, Journal of Applied Physiology 66(4). 1662-1673.

A.

B.

A.

B.

A.

B.

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: primer sequence: porcine AMPKalpha2

<400> SEQUENCE: 1
cgacgtggag ctgtactgct t                                              21

<210> SEQ ID NO 2
<211> LENGTH: 21
<212> TYPE: DNA
<213> ORGANISM: Artificial Sequence
<220> FEATURE:
<223> OTHER INFORMATION: primer sequence: porcine AMPKalpha2

<400> SEQUENCE: 2
cataggtcag gcagaacttg c                                              21

<210> SEQ ID NO 3
<211> LENGTH: 20
<212> TYPE: DNA
<213> ORGANISM: Artificial Sequence
<220> FEATURE:
<223> OTHER INFORMATION: primer sequence: porcine SGLT1

<400> SEQUENCE: 3
cgtgctgttt ccagatgatg                                                20

<210> SEQ ID NO 4
<211> LENGTH: 20
<212> TYPE: DNA
<213> ORGANISM: Artificial Sequence
<220> FEATURE:
<223> OTHER INFORMATION: primer sequence: porcine SGLT1

<400> SEQUENCE: 4
atcagctcca tgaccagctt                                                20

<210> SEQ ID NO 5
<211> LENGTH: 21
<212> TYPE: DNA
<213> ORGANISM: Artificial Sequence
<220> FEATURE:
<223> OTHER INFORMATION: porcine ribosomal protein L32 (housekeeper)

<400> SEQUENCE: 5
```

```
tggaagagac gttgtgagca a                                             21

<210> SEQ ID NO 6
<211> LENGTH: 25
<212> TYPE: DNA
<213> ORGANISM: Artificial Sequence
<220> FEATURE:
<223> OTHER INFORMATION: porcine ribosomal protein L32 (housekeeper)

<400> SEQUENCE: 6
cggaagtttc tggtacacaa tgtaa                                         25
```

METHOD FOR INCREASING PERFORMANCE OF OFFSPRING

CROSS REFERENCE TO RELATED APPLICATIONS

This application is a continuation of U.S. application Ser. No. 13/784,111, filed Mar. 4, 2013, which is a divisional application of U.S. application Ser. No. 12/950,620, filed Nov. 19, 2010, now issued U.S. Pat. No. 8,409,585, which is a continuation of U.S. application Ser. No. 12/738,154, filed Apr. 15, 2010, now abandoned, which is a U.S. national counterpart application under 35 U.S.C. §371 of international application serial No. PCT/US2008/079995, filed Oct. 15, 2008, which claims priority under 35 U.S.C. §119(e) to U.S. Provisional Application No. 60/980,143, filed Oct. 15, 2007, all of which is are expressly incorporated by reference herein.

FIELD OF THE INVENTION

The invention relates to methods for increasing intestinal transport of nutrients in the offspring of an animal, and compositions therefor. The invention also relates to methods for increasing the growth performance of the offspring of an animal, and compositions therefor.

BACKGROUND AND SUMMARY

Omega-3 and omega-6 fatty acids and their metabolites regulate numerous activities in vivo, including inflammation, disease resistance, platelet function and vessel wall contractions. Moreover, supplementation of omega-3 fatty acids and/or gamma-linolenic acid present in the diet of animals and humans are reported to have favorable effects on heart disease, inflammatory and autoimmune disorders, diabetes, renal disease, cancer, and immunity as well as learning, visual acuity and neurological function.

On a cellular level long chain omega-3 fatty acids are readily incorporated into the phospholipid fraction of cell membranes where they influence membrane permeability/fluidity and transport. This represents a storage form of these fatty acids, where they remain until acted upon by phospholipase enzymes which release them for further conversion to eicosanoids.

Linoleic and alpha-linolenic acids are C18-containing fatty acids that are parent compounds of the omega-6 and omega-3 families of fatty acids, respectively. Omega-3 and omega-6 fatty acids undergo unsaturation (i.e., adding double bonds) and sequential elongation from the carboxyl end (i.e., adding 2-carbon units) with the D6-desaturase enzyme being the rate limiting enzyme in metabolism of these long chain fatty acids. The same enzymes are used for these families, making the families antagonistic to one another. Such antagonism, resulting from requirements for the same enzymes, extends into the further metabolism of the C20-containing members of these families into metabolites called eicosanoids.

The polyunsaturated fatty acids, including omega-3 and omega-6 fatty acids, differ from the other fatty acids in that they cannot be synthesized in the body from saturated or monounsaturated fatty acids, but must be obtained in the diet. The omega-6 fatty acid, linoleic acid, is found in high quantities in vegetable oils such as corn, cottonseed, soybean, safflower and sunflower oil. The omega-3 fatty acid, alpha-linolenic acid, is found in high quantities in flaxseed oil, linseed oil, *perilla* oil and canola oil. Other important compounds include arachidonic acid, found in animal fat; gamma-linolenic acid, found in evening primrose oil, borage oil, and blackcurrant oil; and eicosapentaenoic acid, docosahexaenoic acid, and docosapentaenoic acid derived from fish oils and algae. These long-chain fatty acids can be formed in the body by elongation and desaturation of the parent linoleic and alpha-linolenic acids if the parent compounds are supplied in the diet.

Applicants have discovered that supplementation of the diet of animals with polyunsaturated fatty acids, including omega-3 fatty acids, derived from algal sources or from non-algal sources having a high docosahexaenoic acid content, results in positive effects for the offspring of the animal when the mother is fed these compositions containing fatty acids. Interestingly, these compositions cause positive effects for the offspring including increased intestinal transport and increased growth performance, including an increase in growth rate, a reduced feed to weight gain, and an increase in the efficiency of feed utilization.

Methods and compositions for increasing intestinal transport of nutrients in an offspring an animal are described herein. In one embodiment, a method of increasing intestinal transport of nutrients in an offspring of an animal is provided. The method comprises the steps of administering to the animal a feed composition comprising an algal composition comprising omega-3 fatty acids or esters thereof wherein the feed composition as a final mixture comprises about 0.01% to about 60% by weight of the algal composition and wherein the animal is a gestating sow, a postpartum sow, another species of agricultural animal, a companion animal, or a human, and increasing intestinal transport in the offspring of the animal.

In accordance with this embodiment, the algal composition can be in the form of dried algae or an oil derived from the algae and the omega-3 fatty acids can comprise C22 or C20 omega-3 fatty acids. Also in accordance with this embodiment, the feed composition as a final mixture can comprise about 0.01% to about 3.0% by weight, about 0.01% to about 4.0% by weight, about 0.01% to about 1.5% by weight, about 0.01% to about 1.0% by weight, about 0.01% to about 0.8% by weight, about 0.01% to about 0.5% by weight, about 0.01% to about 0.3% by weight, about 0.1% to about 0.5% by weight, about 0.01% to about 18% by weight, about 0.01% to about 20% by weight, about 0.01% to about 30% by weight, about 0.01% to about 40% by weight, about 0.01% to about 50% by weight, or about 0.01% to about 60% by weight of the algal composition.

Also in accordance with this embodiment, the feed composition as a final mixture can further comprise omega-6 fatty acids or esters thereof, the feed composition can be administered during lactation, gestation, or daily to the animal, the feed composition as a final mixture can further comprise an antioxidant, the omega-3 fatty acids in the feed composition can be stabilized by encapsulation, the omega-3 fatty acids can comprise docosahexaenoic acid and eicosapentaenoic acid, and the omega-3 fatty acids can comprise docosahexaenoic acid, eicosapentaenoic acid, and docosapentanoic acid. Further in accordance with this embodiment, the ratio of docosahexaenoic acid to eicosapentaenoic acid can be about 60:1, about 30:1, about 28:1, about 25:1, about 20:1, about 15:1, about 10:1, about 5:1, or about 2:1 the species of agricultural animals can be selected from the group consisting of a chicken, a horse, a pony, a cow, a turkey, a pheasant, a quail, an ovine animal, a goat, an ostrich, and a duck, and the companion animal can be selected from the group consisting of a canine species and a feline species.

In yet another embodiment, a method of increasing intestinal transport of nutrients in a piglet is provided. The method comprises the steps of administering to the piglet a feed composition comprising an algal composition comprising omega-3 fatty acids or esters thereof wherein the algal composition comprises docosahexaenoic acid and eicosapentaenoic acid and the docosahexaenoic acid to eicosapentaenoic acid ratio in the algal composition is about 30:1 to about 1:1, and increasing intestinal transport in the piglet.

In accordance with this embodiment, the algal composition can be in the form of dried algae or an oil derived from the algae, or residuals from dried algae or algal oils, and the omega-3 fatty acids can comprise C22 or C20 omega-3 fatty acids. Also in accordance with this embodiment, the feed composition as a final mixture can comprise about 0.01% to about 3.0% by weight, about 0.01% to about 4.0% by weight, about 0.01% to about 1.5% by weight, about 0.01% to about 1.0% by weight, about 0.01% to about 0.8% by weight, about 0.01% to about 0.5% by weight, about 0.01% to about 0.3% by weight, about 0.1% to about 0.5% by weight, about 0.01% to about 18% by weight, about 0.01% to about 20% by weight, about 0.01% to about 30% by weight, about 0.01% to about 40% by weight, about 0.01% to about 50% by weight, or about 0.01% to about 60% by weight of the algal composition.

Also in accordance with this embodiment, the feed composition as a final mixture can further comprise omega-6 fatty acids or esters thereof, the feed composition can be administered daily to the animal, the feed composition as a final mixture can further comprise an antioxidant, the omega-3 fatty acids in the feed composition can be stabilized by encapsulation, and the omega-3 fatty acids can further comprise docosapentanoic acid. Further in accordance with this embodiment, the ratio of docosahexaenoic acid to eicosapentaenoic acid can be about 30:1, about 28:1, about 25:1, about 20:1, about 15:1, about 10:1, about 5:1, or about 1:1.

In still another embodiment, a method of increasing intestinal transport of nutrients in the offspring of an animal is provided. The method comprises the steps of administering to the animal a feed composition comprising a non-algal composition comprising omega-3 fatty acids or esters thereof wherein the docosahexaenoic acid to eicosapentaenoic acid ratio in the non-algal composition is about 30:1 to about 1:1 and wherein the animal is a species of agricultural animal other than swine, a companion animal, or a human, and increasing intestinal transport in the offspring of the animal.

In accordance with this embodiment, the omega-3 fatty acids can comprise C22 or C20 omega-3 fatty acids. Also in accordance with this embodiment, the feed composition as a final mixture can comprise about 0.01% to about 3.0% by weight, about 0.01% to about 4.0% by weight, about 0.01% to about 1.5% by weight, about 0.01% to about 1.0% by weight, about 0.01% to about 0.8% by weight, about 0.01% to about 0.5% by weight, about 0.01% to about 0.3% by weight, about 0.1% to about 0.5% by weight, about 0.01% to about 18% by weight, about 0.01% to about 20% by weight, about 0.01% to about 30% by weight, about 0.01% to about 40% by weight, about 0.01% to about 50% by weight, about 0.01% to about 60% by weight, about 0.01% to about 70% by weight of the algal composition.

Also in accordance with this embodiment, the feed composition as a final mixture can further comprise omega-6 fatty acids or esters thereof, the feed composition can be administered during lactation, gestation, or daily to the animal, the feed composition as a final mixture can further comprise an antioxidant, the omega-3 fatty acids in the feed composition can be stabilized by encapsulation, and the omega-3 fatty acids can further comprise docosapentanoic acid. Further in accordance with this embodiment, the ratio of docosahexaenoic acid to eicosapentaenoic acid can be about 25:1, about 20:1, about 15:1, about 10:1, about 5:1, or about 2:1, the species of agricultural animals can be selected from the group consisting of a chicken, a horse, a pony, a cow, a turkey, a pheasant, a quail, an ovine animal, a goat, an ostrich, and a duck, and the companion animal can be selected from the group consisting of a canine species and a feline species.

In another illustrative embodiment, a method of increasing the growth performance of an offspring of an animal is provided. The method comprises the steps of administering to the animal a feed composition comprising an algal composition comprising omega-3 fatty acids or esters thereof wherein the algal composition comprises docosahexaenoic acid and eicosapentaenoic acid and the docosahexaenoic acid to eicosapentaenoic acid ratio in the algal composition is about 60:1 to about 1:1 and wherein the animal is a gestating sow, a postpartum sow, another species of agricultural animal, a companion animal, or a human, and increasing the growth performance of the offspring of the animal. In another embodiment, the growth performance is selected from a group consisting of an increased growth rate of the offspring, a reduced feed to weight gain ratio for the offspring, and an increase in the efficiency of feed utilization.

In another aspect, a method is provided of increasing the growth performance of an offspring of an animal. The method comprises the steps of administering to the animal a feed composition comprising an algal composition comprising omega-3 fatty acids or esters thereof wherein the feed composition as a final mixture comprises about 0.01% to about 60% by weight of the algal composition and wherein the animal is a gestating sow, a postpartum sow, another species of agricultural animal, a companion animal, or a human, and increasing the growth performance of the offspring of the animal. In one aspect, the growth performance is selected from a group consisting of an increased growth rate of the offspring and a reduced feed to weight gain ratio for the offspring.

In yet another embodiment, a method is provided of increasing the growth performance of an offspring of an animal. The method comprises the steps of administering to the animal a feed composition comprising a non-algal composition comprising omega-3 fatty acids or esters thereof wherein the docosahexaenoic acid to eicosapentaenoic acid ratio in the non-algal composition is about 30:1 to about 1:1 and wherein the animal is a species of agricultural animal other than swine, a companion animal, or a human, and increasing the growth performance of the offspring of the animal. In this embodiment, the growth performance can be selected from a group consisting of an increased growth rate of the offspring and a reduced feed to weight gain ratio for the offspring.

In still another embodiment, a method is provided of increasing the growth performance of an offspring of an animal. The method comprises the steps of administering to the animal a feed composition comprising a non-algal composition comprising omega-3 fatty acids or esters thereof, wherein the feed composition as a final mixture can comprise about 0.01% to about 90% by weight of the non-algal composition, wherein the animal is a species of agricultural animal, a companion animal, or a human, and increasing the growth performance of the offspring of the animal. In this embodiment, the growth performance can be selected from a group consisting of an increased growth rate of the offspring and a reduced feed to weight gain ratio for the offspring.

In another embodiment, a method is provided of increasing intestinal transport in an offspring of a swine. The method comprises the steps of administering to the swine a feed composition comprising a non-algal composition comprising omega-3 fatty acids or esters thereof wherein the docosahexaenoic acid to eicosapentaenoic acid ratio in the non-algal composition is about 30:1 to about 2:1.

In yet another embodiment, a method is provided of increasing the growth performance in an offspring of a swine. The method comprises the steps of administering to the swine a feed composition comprising a non-algal composition comprising omega-3 fatty acids or esters thereof wherein the docosahexaenoic acid to eicosapentaenoic acid ratio in the non-algal composition is about 30:1 to about 2:1.

DETAILED DESCRIPTION OF THE INVENTION

Figure 1:
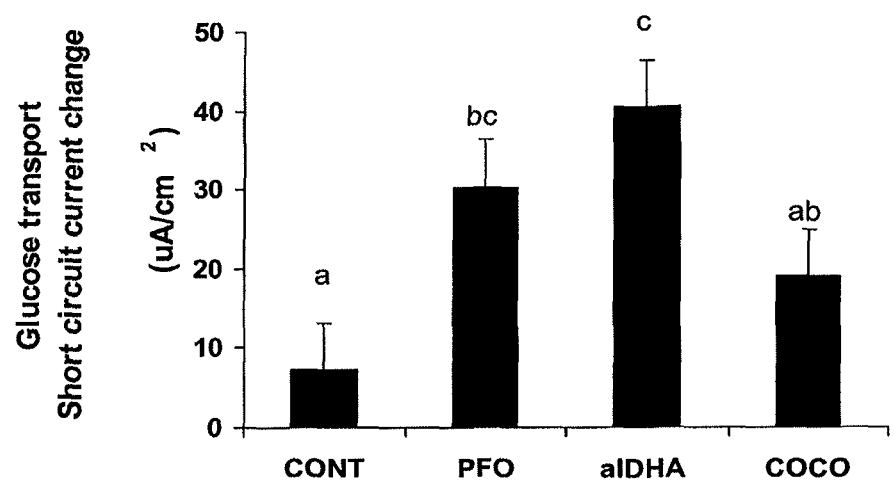
FIG. 1 shows active glucose (panel A) and glutamine (panel B) transport in jejunum samples obtained from piglets weaned at 14-17 days of age from sows fed one of four diets: (1) a basal corn/soybean meal control (no added fat, CONT); (2) the basal diet supplemented with protected fish oil (PFO); (3) the basal diet supplemented with DHA fats from *Schizochytrium* algae (alDHA); or (4) the basal diet supplemented with dried coconut fat (COCO). Piglets (n=4 per treatment) were deprived of feed for 24 hours post-weaning. Means without a common letter differ, P<0.05. Pooled SEM are shown.
Figure 1:
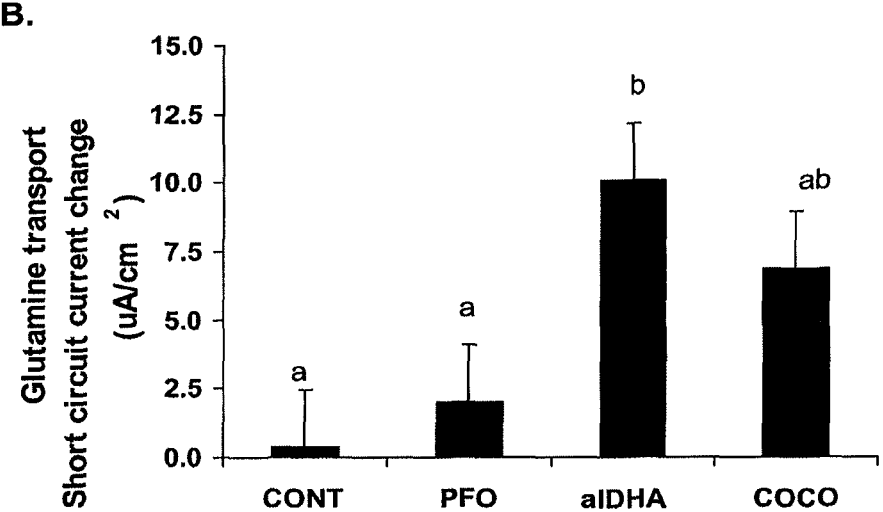

While the invention is susceptible to various modifications and alternative forms, specific embodiments will herein be described in detail. It should be understood, however, that there is no intent to limit the invention to the particular forms described, but on the contrary, the intention is to cover all modifications, equivalents, and alternatives falling within the spirit and scope of the invention.

Methods and compositions for increasing intestinal transport of nutrients in an offspring of an animal are described. More particularly, methods and compositions are described for administration to an animal of a feed composition supplemented with a composition comprising omega-3 fatty acids or esters thereof, to increase the intestinal transport of nutrients in the offspring of the animal. For example, the methods and compositions described herein may increase intestinal transport of nutrients including, but not limited to, vitamins, lipids, minerals, amino acids (e.g., glutamine, etc.), carbohydrates (e.g., glucose, etc.), proteins, and the like. Additionally, the methods and compositions described are useful to increase tissue energy stores (e.g., muscle glycogen units or muscle glycosyl units).

The compositions described herein contain, in particular, a source of omega-3 fatty acids or esters thereof, such as products from algal sources (e.g., algal oils, dried algal products, and residuals and derivatives thereof), non-algal sources (e.g., oils, dried products, and derivatives of non-algal marine sources, as well as nuts, seeds, and plant products), or combinations thereof. The algal and non-algal products serve as a source of omega-3 fatty acids/esters and their metabolites, such as eicosapentaenoic acid (EPA), docosahexaenoic acid (DHA), and docosapentaenoic acid (DPA), or mixtures thereof.

Any source of omega-3 fatty acids may be used in the methods and compositions described herein. In one embodiment, omega-3 fatty acid sources useful in the methods and compositions described herein comprise $C_{22}$ omega-3 fatty acids and/or $C_{20}$ omega-3 fatty acids. In another embodiment, compositions for use as a source of omega-3 fatty acids in the feed composition as a final mixture will have a DHA:EPA ratio≥1:1. In still another illustrative embodiment, the feed composition as a final mixture as described herein comprises DHA and EPA in a DHA:EPA ratio of about 1:1 to about 60:1. In another illustrative embodiment, the final feed compositions as described herein comprise DHA and EPA in a ratio of from about 8:1 to about 30:1, or about 30:1, about 28:1, about 25:1, about 20:1, about 15:1, about 10:1, about 5:1, or about 2:1.

Fatty acids with no double bonds are termed saturated fatty acids, those with one double bond are termed monounsaturated fatty acids, and those with multiple double bonds are termed polyunsaturated fatty acids. Overall digestibility appears to increase with the degree of unsaturation. A convenient shorthand system is used in this specification to denote the structure of fatty acids. This system uses a number denoting the number of carbons in the hydrocarbon chain, followed by a colon and a number indicating the number of double bonds in the molecule, and then by a "w6" or a "w3" to denote "omega-6" or "omega-3", respectively (e.g., 22:5w6). The "w6" or a "w3" denotes the location of the first double bond from the methyl end of the fatty acid molecule. Trivial names in the w6 series of fatty acids include linoleic acid (18:2w6), gamma-linoleic acid (18:3w6), and arachidonic acid (20:4w6). The only fatty acid in the w3 series with a trivial name is alpha-linolenic acid (18:3w3). For the purposes of this application a fatty acid with the nomenclature 20:5w3 is eicosapentaenoic acid, with the nomenclature 22:6w3 is docosahexaneoic acid, and with the nomenclature 22:5w3 is docosapentaenoic acid.

The methods of the present invention utilize an omega-3 fatty acid-containing composition as a source of long chain omega-3 fatty acids, such as eicosapentaenoic acid, docosahexaneoic acid, docosapentaenoic acid, and esters thereof, to increase the intestinal transport of nutrients in an offspring of an animal. The omega-3 fatty acid-containing composition used herein can be obtained from an algal source or a non-algal source. In one embodiment, the feed composition is supplemented with an omega-3 fatty acid-containing composition comprising DHA and EPA, wherein the DHA:EPA ratio in the feed composition as a final mixture is about 1:1 to about 30:1. In one aspect, this feed composition can be fed to piglets. In another embodiment, the DHA:EPA ratio in the final feed composition is about 30:1 to about 2:1. In one illustrative embodiment, the feed composition can contain a non-algal source of omega-3 fatty acids. In yet another embodiment, the DHA:EPA ratio in the final feed composition is about 28:1, about 25:1, about 20:1, about 15:1, about 10:1, about 5:1, or about 2:1.

A biologically effective amount of the omega-3 fatty acid-containing composition can be administered to increase the intestinal transport of nutrients in the offspring of animals. By "biologically effective amount" is meant an amount of the omega-3 fatty acid-containing composition capable of increasing the intestinal transport of nutrients in the offspring of an animal by any mechanism, including those described herein. Additionally, a biologically effective amount of the omega-3 fatty acid-containing composition can be an amount capable of increasing tissue energy stores, and/or an amount effective to increase growth performance (e.g., increasing growth rate, reducing the feed to weight gain ratio, increasing weaning weight, or increasing the efficiency of feed utilization).

In one illustrative embodiment, the feed compositions of the invention that contain omega-3 fatty acids are administered to the animals orally, but any other effective method of administration known to those skilled in the art may be utilized. In illustrative embodiments, the feed composition as a final mixture may comprise an algal derived composition or a non-algal derived composition, such as a non-algal marine product (e.g., fish oil or fish meal), or a nut, seed, or plant derived product (e.g., walnut, flaxseed, canola, soybean oil, or corn oil, or a derivative thereof), or combinations thereof. In illustrative embodiments, the feed composition as a final mixture may be supplemented with any omega-3 fatty acid-containing composition, and may include, for example, an algal oil, a dried algal product (including dried whole cells and ground algal products), a fish oil (e.g., salmon oil or another fish oil from a North Atlantic cold water fish), fish meal, or an oil derived from fish meal, or a mixture thereof, or residuals from any of these sources of omega-3 fatty acids to provide a source of omega-3 fatty acids/esters in a mixture with an art-recognized animal feed blend.

In one illustrative aspect, the feed composition as a final mixture may be administered to the animal for any time period that is effective to increase the intestinal transport of nutrients in the offspring of the animal. For example, the feed composition may be fed to a female animal daily for the lifetime of the animal. Alternatively, the feed composition may be administered to the animal for a shorter time period. In one embodiment, the feed composition can be administered to a gestating sow, a postpartum sow, a piglet, another species of agricultural animal, a companion animal, or a human (e.g., to increase the longevity of the human or the animal). Illustratively, the companion animal, the human, or the species of agricultural animal may be a gestating, a lactating, or a postpartum animal.

In another embodiment, the feed composition is administered to a postnatal animal, including a nursing animal or an animal being weaned or an animal after weaning. In another embodiment, the feed composition can be administered to a prenatal animal in utero by feeding the composition to a gestating mother. In yet another embodiment, the feed composition can be administered to a nursing animal by feeding the composition to a lactating mother, or alternatively, by feeding the composition directly to the nursing animal through a prepared diet (e.g., a formula). The time periods for administration of the feed composition described above are nonlimiting and it should be appreciated that any time period determined to be effective to increase the intestinal transport of nutrients in the offspring of the animal may be used.

In one embodiment, as described herein, a species of agricultural animal other than a pig may be fed the feed composition and those species may include bovine species (e.g., cattle and bison), equine species (e.g., horses, ponies, and donkeys), ovine species (e.g., sheep), caprine species (e.g., goats), rabbits, and poultry (e.g., chickens, turkeys, pheasant, ducks, ostrich, emu, quail, and geese). As used herein, a species of agricultural animal other than a pig may include any animal that is raised for personal use (e.g., for providing food, fuel, etc.) or for profit. In yet another embodiment, a companion animal may be fed the compositions described herein and a companion animal include any animal that is kept or raised for companionship purposes, for example, canine and feline species.

In various illustrative embodiments, any animal feed blend known in the art may be used to make the feed composition such as rapeseed meal, flaxseed meal, cottonseed meal, soybean meal, and cornmeal. The animal feed blend can be supplemented with an omega-3 fatty acid-containing composition, but other ingredients may optionally be added to the animal feed blend. Optional ingredients of the animal feed blend include sugars and complex carbohydrates such as both water-soluble and water-insoluble monosaccharides, disaccharides and polysaccharides. Optional amino acid ingredients that may be added to the feed blend are arginine, histidine, isoleucine, leucine, lysine, methionine, phenylalanine, threonine, tryptophan, valine, tyrosine ethyl HCl, alanine, aspartic acid, sodium glutamate, glycine, proline, serine, cysteine ethyl HCl, and analogs, and salts thereof. Vitamins that may be optionally added are thiamine HCl, riboflavin, pyridoxine HCl, niacin, niacinamide, inositol, choline chloride, calcium pantothenate, biotin, folic acid, ascorbic acid, and vitamins A, B, K, D, E, and the like. Optional lipid blends of animal or plant origin or fibrous ingredients could also be added. Protein ingredients may also be added and include protein obtained from meat meal or fish meal, liquid or powdered egg, fish solubles, and the like. Any medicament ingredients known in the art may also be added to the animal feed blend such as antibiotics.

In an illustrative embodiment, antioxidants may be added to the feed composition to prevent oxidation of the fatty acids present in the omega-3 fatty acid-containing composition used to supplement the feed composition, such as the omega-3 long chain fatty acids, eicosapentaenoic acid, docosahexaneoic acid, and docosapentaenoic acid. Oxidation of fatty acids occurs over time and may be affected by such conditions as moisture and the presence of mineral catalysts and by such characteristics of fatty acids as the number of double bonds and positioning and configuration of bonds. Oxidation of these omega-3 fatty acids can be prevented by the introduction of naturally-occurring antioxidants, such as beta-carotene, vitamin E, vitamin C, and tocopherol or of synthetic antioxidants such as butylated hydroxytoluene, butylated hydroxyanisole, tertiary-butylhydroquinone, propyl gallate or ethoxyquin to the feed composition. Compounds which act synergistically with antioxidants can also be added such as ascorbic acid, citric acid, and phosphoric acid. The amount of antioxidants incorporated in this manner depends on requirements such as product formulation, shipping conditions (e.g., shipping under a nitrogen blanket), packaging methods, and desired shelf life.

In one embodiment, the omega-3 fatty acid-containing composition used to supplement the feed composition is derived from a high purity algal preparation that comprises a high content of DHA. In one aspect, the algal preparation may comprise a high DHA:EPA ratio, i.e., the amount of DHA in the composition can be greater than or equal to the amount of EPA in the composition (e.g., up to a 60:1 ratio of DHA:EPA). In an alternative embodiment, no EPA is present in the algal composition. Various ratio embodiments are described herein. In one embodiment, the feed composition as a final mixture can be supplemented with an omega-3 fatty acid-containing composition derived from algae, such as oils, gels, pastes, dried products, and residuals or derivatives thereof. In other embodiments, the omega-3 fatty acid-containing composition may include whole algal cell products, ground algal products, or residual products remaining from the production of oils, gels, pastes, and dried products, or derivatives thereof. In illustrative aspects, the algal product may be obtained from any algal source, including marine or freshwater algal sources.

In various embodiments, the algal sources may include, but are not limited to, species of *Schizochytrium, Spirulina, Chlorella, Chaetoceros, Cyclotella, Isochrysis, Nonnocholoropsis, Nitzschia, Phyaeodactylum*, as well as dinoflagellates, including species of *Amphidinium, Ceratium, Cochlodinium, Crypthecodinium* (e.g., *Crypthecodinium cohnii*), *Gonyaulax*, and *Peridinium*. In another embodiment, the omega-3 fatty acid-containing composition derived from algae may include a composition derived from a genetically modified organisms, modified by expression of an algal gene. Any non-toxic algal source capable of increasing intestinal transport of nutrients in an animal may be used. In various embodiments, algal products as herein described provide a source of omega-3 polyunsaturated long chain fatty acids including eicosapentaenoic acid (20:5w3), docosahexaneoic acid (22:6w3), and docosapentaenoic acid (22:5w3). In various illustrative embodiments, the omega-3 fatty acid-containing composition derived from algae has a DHA:EPA ratio≥1:1, ≥5:1, ≥10:1, ≥15:1, ≥20:1, or ≥25:1.

In another embodiment, the animal feed blend is supplemented with an omega-3 fatty acid-containing composition derived from a non-algal source, such as fish oils or fish meal, as well as plant, nut, or seed oils, or a derivative thereof, or a combination thereof. The omega-3 fatty acid-containing composition derived from a non-algal source may also include compositions derived from a genetically modified organism. For example, genetically modified plants, including transgenic plants, may be used as a non-algal source of omega-3 fatty acids. In addition, nutritionally enhanced plants or seeds may be used as a non-algal source of omega-3 fatty acids. Examples of plants that may be genetically modified or nutritionally enhanced for use as a non-algal source include, but are not limited to, corn, canola, soybean, flax, rapeseed, and hominy.

The non-algal oils described herein may be obtained from any source. In one embodiment, the non-algal oil source is North Atlantic cold water fish. Fish oils provide a source of both omega-3 and omega-6 fatty acids, but are a particularly good source of omega-3 polyunsaturated fatty acids. The omega-3 polyunsaturated long chain fatty acids eicosapentaenoic acid (20:5w3), docosahexaneoic acid (22:6w3), and docosapentaenoic acid (22:5w3) are typical of fish oils and together comprise about 25-38% by weight of the fish oil. Omega-6 polyunsaturated fatty acids present in fish oils include linoleic acid and arachidonic acid and are present at lesser concentrations of about 10% by weight.

Oils are understood to be lipids or fats including the glyceride esters of fatty acids along with associated phosphatides, sterols, alcohols, hydrocarbons, ketones, alkyl esters, salts, and related compounds. Further, as described herein, dried products include algal and non-algal products prepared by any method known in the art, and may include spray-dried or freeze-dried products. The algal and non-algal compositions described herein may include whole cell products, ground products, or residuals or derivatives thereof.

In various illustrative aspects, the oils or fatty acid ester components may be added in an unprocessed form or in pure form, or may be conjugated or unconjugated, including supplements (e.g., conjugated linoleic acids). Illustratively, the fatty acid esters added to the feed composition may be triglycerides, diglycerides, monoglycerides, phospholipids, lysopholipids, or can be chemically beneficiated or enzymatically beneficiated for enhanced content of desired fatty acid esters.

In one embodiment, the feed compositions described herein may also comprise omega-6 fatty acids or esters thereof, as described in U.S. Pat. No. 7,084,175 and U.S. patent application Ser. No. 10/142,685, incorporated herein by reference. Illustratively, the omega-6 fatty acids usable in the present invention can be unsaturated fatty acids having at least two carbon-carbon double bonds such as 2,4-decadienoic acid, linolenic acid, gamma-linolenic acid, 8,10,12-octadecatrienoic acid and arachidonic acid. In another embodiment, the omega-6 fatty acid can be gamma-linolenic acid. In other embodiments, omega-6 fatty acids/esters for use in the feed composition of the present invention include omega-6 fatty acids/esters derived from an art-recognized meal such as corn meal or soybean meal or from oils such as corn oil, cottonseed oil, soybean oil, safflower oil, sunflower oil, linseed oil, borage oil, blackcurrant oil, evening primrose oil, and the like.

In one illustrative aspect, the feed composition described herein is supplemented with concentrations of an omega-3 fatty acid-containing composition, such as algal oil, gel, paste, dried products, or a combination thereof, or residuals thereof, sufficient to provide amounts of omega-3 fatty acids/esters in the feed composition as a final mixture that are effective in increasing the intestinal transport of nutrients in the offspring of an animal. Alternatively, the feed composition may be supplemented with an omega-3 fatty acid-containing composition, such as fish oil, fish meal, plant-derived products, or combinations thereof, sufficient to provide amounts of omega-3 fatty acids/esters in the feed composition as a final mixture that are effective in increasing the intestinal transport of nutrients in the offspring of an animal. In another embodiment, the feed composition may be supplemented with a combination of algal and non-algal omega-3 fatty acid-containing sources.

In one illustrative embodiment, the feed composition can be supplemented with an omega-3 fatty acid-containing composition in an amount of about 0.01% to about 60% by weight of the feed composition as a final mixture. In another embodiment the feed composition can be supplemented with an omega-3 fatty acid-containing composition in an amount of about 0.1% to about 0.5% by weight of the feed composition as a final mixture. In yet another embodiment, the feed composition can be supplemented with an omega-3 fatty acid-containing composition in an amount of about 0.01% to about 0.3% by weight, about 0.01% to about 0.5% by weight, about 0.01% to about 0.8% by weight, about 0.01% to about 1.0% by weight, about 0.01% to about 1.5% by weight, about 0.01% to about 3.0% by weight, about 0.01% to about 4.0% by weight, about 0.01% to about 18% by weight, about 0.01% to about 20% by weight, about 0.01% to about 30% by weight, about 0.01% to about 40% by weight, about 0.01% to about 50% by weight, about 0.01% to about 60% by weight, about 0.01% to about 70% by weight, or about 0.01% to about 90% by weight of the feed composition as a final mixture.

In each of these embodiments it is to be understood that the percentage of the omega-3 fatty acid-containing composition by weight of the feed composition refers to the final feed composition (i.e., the feed composition as a final mixture) containing the animal feed blend, the omega-3 fatty acid-containing composition (e.g., algal oil, ground algae or other dry algal product, or residuals thereof, or fish oil, etc.), and optionally added ingredients. In such embodiments of the invention, the omega-3 fatty acid-containing composition may be derived from any type of algal or non-algal source.

In various aspects, the omega-3 fatty acid-containing composition as described herein may be administered in an unencapsulated or an encapsulated form in a mixture with an animal feed blend. Encapsulation protects the omega-3 fatty acids/esters and omega-6 fatty acids/esters from breakdown and/or oxidation prior to digestion and absorption of the fatty acids/esters by the animal (i.e., encapsulation increases the stability of fatty acids) and provides a dry product for easier mixing with an animal feed blend. The omega-3 fatty acids/esters and omega-6 fatty acids/esters can be protected in this manner, for example, by coating the oil with a protein or any other substances known in the art to be effective encapsulating agents such as polymers, waxes, fats, and hydrogenated vegetable oils. For example, an oil or other algal or non-algal product, may be encapsulated using an art-recognized technique such as a $Na^{2+}$-alginate encapsulation technique wherein the oil is coated with $Na^{2+}$-alginate followed by conversion to $Ca^{2+}$-alginate in the presence of $Ca^{2+}$ ions for encapsulation. Alternatively, the oil or other algal or non-algal product may be encapsulated by an art-recognized technique such as enrobing the fatty acids to stabilize the fatty acids or prilling (i.e., atomizing a molten liquid and cooling the droplets to form a bead). For example, the oil or other algal or non-algal product may be prilled in hydrogenated cottonseed flakes or hydrogenated soy bean oil to produce a dry oil. In various embodiments, the oil or other algal or non-algal product may be used in an entirely unencapsulated form, an entirely encapsulated form, or mixtures of unencapsulated and encapsulated oil may be added to the feed composition.

In various embodiments, the feed compositions described herein, when fed to in utero through the mother (e.g., a gestating sow) and/or to postnatal animals (e.g., by lactation through a postpartum sow or directly to the postnatal animal), may result not only in increases in intestinal transport, but also in benefits regarding insulin sensitivity, and in increases in growth performance of the postnatal animals (e.g., a piglet). Any of the embodiments described above can be used to increase the growth performance (e.g., increased growth rate, reduced feed to weight gain ratio, or increased efficiency of feed utilization) of the offspring of an animal.

Accordingly, in one embodiment, a method for increasing growth performance of the postnatal animal is provided. The method comprises the step of administering to the postnatal animal or the mother a feed composition comprising an algal composition comprising omega-3 fatty acids or esters thereof wherein the feed composition as a final mixture comprises about 0.01% to about 60% by weight of the algal composition and wherein the animal is a sow, a piglet, another species of agricultural animal, a companion animal, or a human.

In accordance with this embodiment, the algal composition can be in the form of dried algae or an oil derived from the algae, or a residual of either composition, and the omega-3 fatty acids can comprise $C_{22}$ or $C_{20}$ omega-3 fatty acids. Also in accordance with this embodiment, the feed composition as a final mixture can comprise about 0.01% to about 3.0% by weight, about 0.01% to about 4.0% by weight, about 0.01% to about 1.5% by weight, about 0.01% to about 1.0% by weight, about 0.01% to about 0.8% by weight, about 0.01% to about 0.5% by weight, about 0.01% to about 0.3% by weight, about 0.1% to about 0.5% by weight, about 0.01% to about 18% by weight, about 0.01% to about 20% by weight, about 0.01% to about 30% by weight, about 0.01% to about 40% by weight, about 0.01% to about 50% by weight, or about 0.01% to about 60% by weight of the algal composition.

Also in accordance with this embodiment, the feed composition as a final mixture can further comprise omega-6 fatty acids or esters thereof, the feed composition can be administered during lactation, or daily to the animal, the feed composition as a final mixture can further comprise an antioxidant, the omega-3 fatty acids in the feed composition can be stabilized by encapsulation, the omega-3 fatty acids can comprise docosahexaenoic acid and eicosapentaenoic acid, and the omega-3 fatty acids can comprise docosahexaenoic acid, eicosapentaenoic acid, and docosapentanoic acid. Further in accordance with this embodiment, the ratio of docosahexaenoic acid to eicosapentaenoic acid can be about 60:1, about 30:1, about 25:1, about 20:1, about 15:1, about 10:1, about 5:1, about 2:1, or about 1:1, the species of agricultural animals can be selected from the group consisting of a chicken, a horse, a pony, a cow, a turkey, a pheasant, a quail, an ovine animal, a goat, an ostrich, and a duck, and the companion animal can be selected from the group consisting of a canine species and a feline species.

This embodiment of the invention can also comprise method embodiments where the postnatal animal is fed a feed composition supplemented with a non-algal source of omega-3 fatty acids under any of the conditions described above where the DHA:EPA ratio is about 30:1 to about 1:1.

While certain embodiments of the present invention have been described and/or exemplified below, it is contemplated

EXAMPLE 1

Animals and Experimental Design

Twenty dams (Ausgene Line 20 dams×SPI sixes) were fed one of four experimental diets for approximately 150 days prior to farrowing (Table 1). The four experimental dietary treatments consisted of (1) basal corn/soybean meal control (no added fat, "CONT"); (2) the basal diet supplemented with protected fish oil (FERTILIUM™ or GROMEGA365™; JBS United Inc., Sheridan, Ind. [i.e., PFO]); (3) the basal diet supplemented with DHA fats from *Schizochytrium* algae (alDHA); (4) the basal diet supplemented with dried coconut fat (COCO).

The fatty acid profiles of the diets are presented in Table 2. Both the protected fish oil and alDHA ingredients had high (n-3) PUFA concentrations and contained 29 and 43% total fat, respectively. The rest of these ingredients comprised of protein and carbohydrate. alDHA contained 40% DHA and 2% EPA by percentage of fat, while PFO had approximately 13% EPA and 13% DHA. The total fat of the four diets differed. However, the DHA percentage of the alDHA diet was equal to the DHA percentage in the PFO diet. The raw COCO fat ingredient was comprised of 88% saturated fat (high in saturated fatty acids C10:0-C16:0) as a percentage of fat. All diets (Table 1) met and exceeded the nutrient requirements for gestating and lactating sows [see NCR, Nutritional Requirements of Swine, $10^{th}$ ed., Washington, D.C.: Natl. Acad. Press (1998)] and all piglets had access to water at all times.

While farrowing in two replicate groups over two weeks, litters were standardized to ten piglets per litter within 24 hours of birth, with cross fostering only occurring within treatment. Subsequently, at 14-17 days of age, one medium size piglet (4.1 kg±0.49) per litter was randomly separated from the dam, grouped penned with piglets from other litters, and fasted overnight to simulate the weaning process (total n=4 per treatment). Following the simulated weaning, piglets were killed by captive bolt gun followed by immediate exsanguination and tissues excised. Small intestinal jejunum, liver and muscles samples were collected and snap frozen in liquid nitrogen and jejunum samples placed in 10% formalin for subsequent analysis.

EXAMPLE 2

Fatty Acid Analysis

One week post farrowing, approximately 40 mL of mid-lactation milk was obtained from four sows of each dietary treatment following an i.v. injection of 10 IU of oxytocin-S (Intervet, Millsboro, Del. USA) to induce milk secretion. At random, several udders from each sow were milked, pooled together and snap frozen on dry ice pending fatty acid analysis. Lipids from milk, muscle and liver samples were extracted by the method of Lepage and Roy [*J. Lipid Res.*, 27: 114-120 (1986), incorporated herein by reference] with minor modifications. Briefly, 0.5 g of tissue or 300 µL of milk were homogenized in 2.5 mL 4:1 methanol:hexane and 200 µL of 3.7 mmol heptadecanoic acid/L methanol was added to each sample as an internal standard.

Fatty acid methyl esters were analyzed by gas chromatography on a Hewlett-Packard model 6890 (Hewlett-Packard, Palo Alto, Calif.) fitted with a Omegawax 320 (30 m×0.32 mm ID, 0.25 µm) capillary column (Sigma-Aldrich, St Louis, Mo. USA). Hydrogen was the carrier gas. The temperature program ranged from 80° C. to 250° C. with a temperature rise of 5° C./min. The injector and detector temperatures were 250° C. and 1 µL of sample was injected and run splitless. Fatty acids were identified by their retention times on the column with respect to appropriate standards.

Feeding gestating and lactating dams the CONT, PFO, alDHA or COCO diets, which varied considerably in their fatty acid profiles, changed the fatty acid composition of the milk accordingly (Table 3). The PFO and alDHA diets had the highest (n-3) fatty acid proportions, thus reflecting each particular ingredient's DHA and EPA concentration. As a result, milk from dams fed the CONT and COCO diets had higher (n-6):(n-3) fatty acid ratios than that from dams fed the other two diets. Additionally, milk from the sows fed the COCO diet was higher in total saturated fatty acids compared to the PFO and alDHA, but not compared to the CONT milk (P<0.05, Table 3). Of the saturated fatty acids found in the sow's milk, C12:0 was six-fold higher in the COCO compared to the CONT or (n-3) PUFA milk samples (P<0.05, Table 3).

Piglet small intestine and muscle fatty acids profiles are outlined in Table 4. The (n-3) PUFA fatty acid supplementation via the PFO maternal diet increased piglet small intestine and muscle total (n-3) PUFA concentration, 200 and 400%, respectively, vs. the CONT group (Table 4). This increase reflected the DHA and(or) EPA percentage of the sows' diets (Table 2) and milk (Table 3), and corresponded significantly with decreased (n-6):(n-3) ratios in all tissues tested (Table 4).

EXAMPLE 3

Ussing Chamber

Proximal jejunum samples starting 40 cm from the stomach consisting of a 20-30 cm segment of proximal jejunum were removed and placed in chilled Krebs-Henseleit buffer (consisting in mmol/L: 25 $NaHCO_3$, 120 NaCl, 1 $MgSO_4$, 6.3 KCl, 2 CaCl, 0.32 $NaH_2PO_4$; pH 7.4) for transport back to the laboratory (<40 min) under constant aeration until clamped in the Ussing chambers. Two jejunal segments per pig were then stripped of outer muscle layers and immediately mounted in Ussing Chambers (DVC 1000 World Precision Instruments, New haven, CT USA).

Each segment was bathed on its mucosal and serosal surfaces (opening area 1.0 $cm^2$) with 8 mL Krebs solution and gassed with 95% $O_2$-5% $CO_2$ mixture. The intestinal segments were voltage clamped at zero mV by an external current after correction for solution resistance. After a 30 minute period to allow the tissues to stabilize, they were challenged independently with 10 mmol/L D-Glucose and 10 mmol/L L-glutamine which was added to serosal buffer, with equimolar (10 mmol/L) mannitol added on the mucosal side.

Potential difference across the tissue was measured for 30 min after each challenge by open circuit conditions every 10 seconds due to a short-circuit current being delivered by a voltage clamp apparatus. The change in maximal current was recorded and the tissue conductance was calculated from the short-circuit current and potential difference using ohm's law. This was repeated on four different days with a total of four pigs per treatment.

Ex-vivo jejunal nutrient absorption following the addition of 10 mmol/L D-glucose or L-glutamine was evaluated in three ways: (1) short circuit current, which measures change in active ion transport; (2) conductance, which measures changes in total ion transport; and (3) passive ion transport, which is measured by changes in resistance.

Active transport was significantly greater following the addition of D-glucose in tissue obtained from piglets of dams fed the alDHA and PFO diets vs. CONT piglets (P<0.05, FIG. 1, panel A). However, only the alDHA treatment glucose transport significantly higher than in the COCO piglets (P<0.05, FIG. 1, panel A). Compared with CONT tissues, active D-glucose uptake of tissue from alDHA piglets was 470% higher, but the PFO and COCO diets also resulted in greater uptake vs. the CONT (320% and 40%, respectively). See also FIG. 5. However, active L-glutamine uptake was only higher in tissue from piglets of dams fed the alDHA diet as compared with CONT and PFO piglets (FIG. 1, panel B). Neither total nor passive ion transport was affected by (n-3) PUFA or COCO dietary supplementation (data not shown)

EXAMPLE 4

Determination of Muscle and Liver Glycogen

Samples of muscle (longissimus dorsi) or liver tissue (0.5 g) were extracted in ice cold perchloric acid (0.5 mol/L) using a Tissue Tearor homogenizer. Duplicate samples (300 µL) of each homogenate were then prepared for glycogen hydrolysis with 0.3 g/L amyloglucosidase (Sigma-Aldrich, St Louis, Mo. USA) for 120 minutes at 38° C. The incubation was stopped by the addition of 0.6 mol/L perchloric acid and the samples clarified by centrifugation (1,500×g, 15 minutes at 4° C.). Glucose (HK) assay kits (Sigma-Aldrich, St Louis, Mo. USA) were used to determine total micromolar glycosyl units (glucose, glucose-6-P, and glucose from glycogen) from the clarified samples and from the original homogenate (glucose, glucose-6-P only). Results were expressed as mg glycosyl units per g wet tissue.

Figure 4:
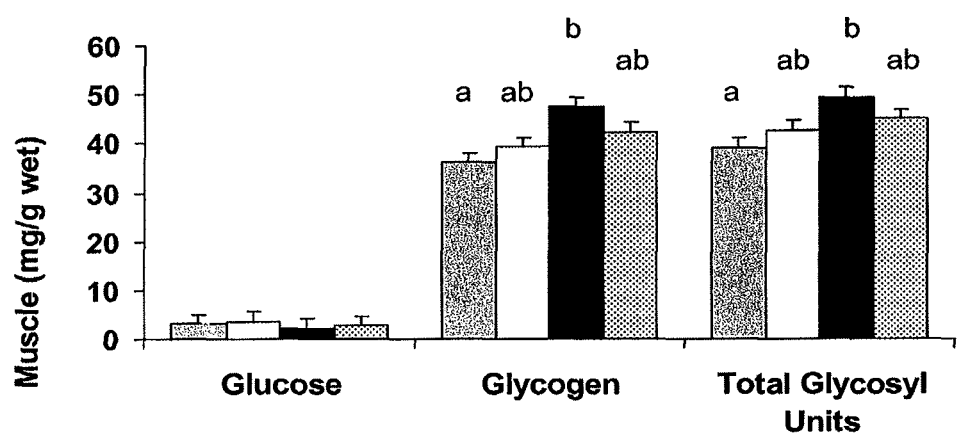
FIG. 4 shows glucose, glycogen and total glycosyl concentrations in longissimus muscle (panel A) and liver (panel B) samples obtained from piglets weaned at 14-17 days of age. The piglets were from sows fed: (1) a basal corn/soybean meal control (no added fat, CONT); (2) the basal diet supplemented with protected fish oil (PFO); (3) the basal diet supplemented with DHA fats from *Schizochytrium* algae (alDHA); or (4) the basal diet supplemented with dried coconut fat (COCO). Piglets (n=4 per treatment) were deprived of feed for 24 hours post-weaning. Different letters represent significant differences (P<0.05). Pooled SEM are shown.
Figure 4:
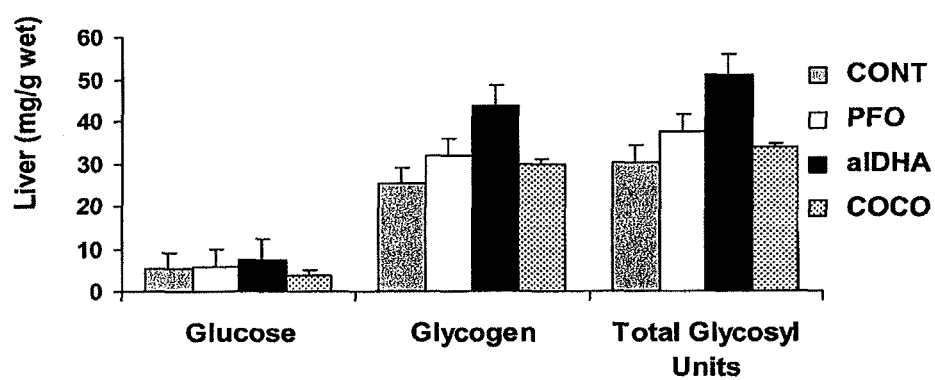

Although muscle glucose concentrations were not altered by dietary treatment (FIG. 4, panel A), glycogen and total glycosyl units were increased (P=0.05) in piglets of dams fed the alDHA diet vs. the CONT diet. In contrast, concentrations were unchanged in piglets of dams fed the PFO and COCO diets. As with muscle, liver glycogen and total glycosyl units in piglets from dams fed the alDHA diet tended to be higher (P=0.089, FIG. 4, panel B). Neither of the (n-3) PUFA diets, nor the COCO diet, altered liver glucose concentrations as compared with the CONT.

EXAMPLE 5

RNA Extraction and Quantitative PCR

Total RNA was recovered from cells using Trizol reagent (Invitrogen, Carlsbad, Calif. USA), DNase treated using the Turbo DNase® (Ambion; Houston, Tex. USA) and total RNA (2 µg) was reverse transcribed using the iScript cDNA synthesis kit (BioRad; Hercules, Calif. USA).

Primer sequences were: porcine AMPKα2, 5'-cgacgtg-gagctgtactgctt-3' [SEQ ID NO: 1] and 5'-cataggtcaggcagaact-tgc-3' [SEQ ID NO: 2], porcine SGLT1, 5'-cgtgctgtttccagat-gatg-3' [SEQ ID NO: 3] and 5'-atcagctccatgaccagctt-3' [SEQ ID NO: 4], and porcine ribosomal protein L32 (housekeeper), 5'-tggaagagacgttgtgagcaa-3' [SEQ ID NO: 5] and 5'-cg-gaagtttctggtacacaatgtaa-3' [SEQ ID NO: 6], all sequences are sense and anti-sense respectively.

Thermal cycler conditions for PCR reactions were 95° C. for 3 min followed by 40 cycles of 95° C. for 15 s, 65° C. for 30 s, and 72° C. for 30 s. Polymerase chain reaction products amplified were cloned into pGEMT vector (Promega, Madison, Wis. USA) and sequenced for verification. Real-time reactions were carried out on an iCycler real-time machine using the IQ™ SYBR Green Supermix kit (BioRad, Hercules, Calif. USA). Abundance of gene product was calculated by regressing against the standard curve generated in the same reaction by their respective plasmids and gene values normalized to ribosomal protein L32 (RPL32) housekeeper gene which was not affected by the dietary treatment (P>0.10).

Figure 2:
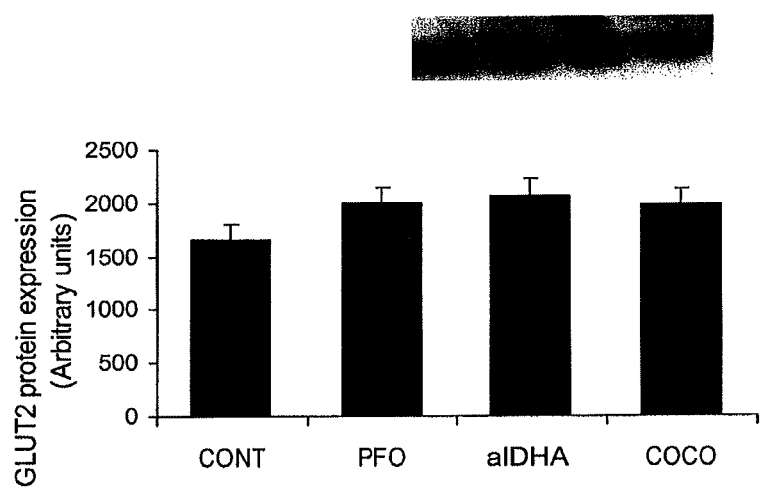
FIG. 2 shows GLUT2 protein expression in jejunum samples obtained from piglets weaned at 14-17 days of age. The piglets were from sows fed: (1) a basal corn/soybean meal control (no added fat, CONT); (2) the basal diet supplemented with protected fish oil (PFO); (3) the basal diet supplemented with DHA fats from *Schizochytrium* algae (alDHA); or (4) the basal diet supplemented with dried coconut fat (COCO). Piglets (n=4 per treatment) were deprived of feed for 24 hours post-weaning and pooled SEM are shown.
Figure 3:
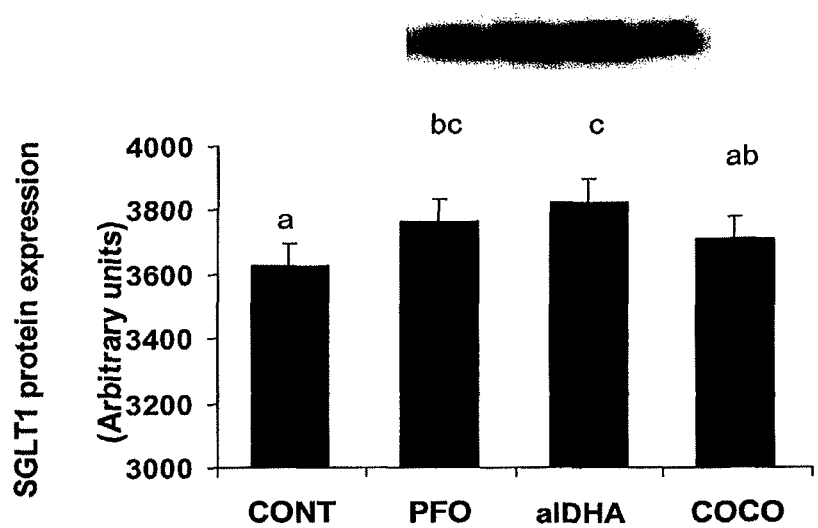
FIG. 3 shows SGLT1 protein expression in jejunum samples obtained from piglets weaned at 14-17 days of age. The sows were fed: (1) a basal corn/soybean meal control (no added fat, CONT); (2) the basal diet supplemented with protected fish oil (PFO); (3) the basal diet supplemented with DHA fats from *Schizochytrium* algae (alDHA); or (4) the basal diet supplemented with dried coconut fat (COCO). Piglets (n=4 per treatment) were deprived of feed for 24 hours post-weaning. Means without a common letter differ, P<0.05. Pooled SEM are shown.

To confirm the increased glucose uptake in (n-3) PUFA treatments and to validate a potential mechanism, total GLUT2 and SGLT1 protein expression and the SGLT1 mRNA abundance in the jejunum was examined. Compared with the CONT piglet jejunum, semi-quantitative immunoblot analysis showed that PFO, alDHA and COCO treatment piglets tended to have greater total GLUT2 protein expression by approximately 20% (P=0.095, FIG. 2). Moreover, both the PFO and alDHA diets resulted in significantly higher total protein expression of SGLT1 as compared with piglets from dams fed the CONT diet (P<0.05, FIG. 3), whereas there was no effect of the COCO diet. See also FIGS. 6 and 7. Quantitative PCR was also conducted to determine whether the mRNA abundance (i.e., log starting quantity) of SGLT1 was also influenced by maternal diet. Dietary fatty acid supplementation did not alter SGLT1 mRNA expression in the jejunum (data presented as log starting quantity for CONT (1.87), PFO (1.71), alDHA (1.84) and COCO (1.70), pooled SEM=0.14).

EXAMPLE 6

Protein Expression

Whole frozen jejunum sections (1 g) were and homogenized on ice in 700 µL Buffer A (50 mmol/L Tris-HCl pH 7.5, 50 mmol/L NaF, 5 mmol/L Sodium Pyrophosphate, 1 mmol/L EDTA, 1 mmol/L DTT, 0.1 mmol/L Phenylmethyl-sulfonyl fluoride, 10% glycerol) containing 1% Triton X-100, 5 µmol/L aprotinin, leupeptin, and pepstatin. The lysates were centrifuged at 6,000×g for 20 minutes at 4° C. to remove insoluble material. Supernatants were collected and protein was quantified using BCA reagents (Pierce, Rockford, Ill. USA) and frozen until assayed. Jejunum lysates were used for both the AMPK assay and western blot analysis.

The abundance of GLUT2 (~60 kDa) and SGLT1 (~70 kDa) protein was determined by western blot analysis. Briefly, supernatant containing 250 µg protein were immunoprecipitated at room temperature for 2 hours using the Catch and Release v2.0 Reversible Immunoprecipitation System (Upstate Cell Signaling Solutions, Charlottesville, Va. USA). Both GLUT2 and SGLT1 were immunoprecipitated with 1:100 primary antibody (Chemicom International, Temecula, Calif. USA) dilutions. Immunoprecipitated proteins were separated by SDS-PAGE using a 12% resolving gel and transferred to a nitrocellulose membrane and probed with primary antibody for GLUT2 or SGLT1 (1:1000) overnight. The membranes were probed with Goat-Anti-rabbit IgG-HRP antibody (Pierce, Rockford, Ill. USA) at 1:20,000 for 1 h at room temperature. Blots were developed using the SuperSignal West Pico Chemiluminescent Substrate system (Pierce, Rockford, Ill. USA), captured onto micro-film for analysis and densitometry of the protein determined using Quantity One 1-D analysis software (Bio-Rad, Hercules, Calif. USA).

EXAMPLE 7

Statistical Analysis

All data are presented as means±pooled SEM. The effects of fatty acids were tested by the PROC MIXED procedure in SAS (Version 9.1, SAS Institute, Cary, N.C.) and treatment differences were evaluated using least significant differences, which provided all pair-wise comparisons. Litter/piglet was considered the experimental unit and experimental replicate or day of harvest was considered a random effect. Differences were deemed significant when P<0.05, and tendencies were noted at P<0.10.

EXAMPLE 8

Animals and Experimental Design

Thirty two females (Ausgene Line 20 dam×SPI sire) were fed one of two experimental diets for approximately 150 days to encompass the entire gestation period or 17-19 days over the lactation period before weaning. The dietary treatments (Table 5) consisted of the following: 1) basal corn/soybean meal control (no added fat, CONT); or 2) the basal diet supplemented with a protected fish oil product ([PFO], Gromega 365™; JBS United Inc., Sheridan, Ind.). The PFO product contains 29% of total fat as n-3 PUFA, with approximately 13% as EPA and 13% as DHA. The gestation and lactation diets were formulated to meet or exceed all the requirements for gestating and lactating sows [NRC, Nutritional Requirements of Swine, 10$^{th}$ ed., Natl. Acad. Press, Washington, D.C. (1998)]. Dams and piglets had access to water at all times.

At farrowing after approximately 150 days on the gestation diets, litters were standardized to ten piglets per dam. To accomplish exposing the piglets to the n-3 fatty acids only during the gestation or suckling (lactation) period, litters were reciprocally switched such that dams fed the CONT diet received piglets from a dam fed the PFO diet, and vice versa for 15-19 days. The four treatments now consisted of gestation/lactation feeding to give CONT/CONT, CONT/PFO, PFO/PFO or PFO/CONT piglets. At 15-19 days of age, one medium size piglet (5.4±0.50 kg) per litter was randomly transferred to a separate room from the dams, grouped penned and fasted overnight to simulate the weaning process (total n=6 per treatment). The following morning, piglets were euthanized and tissue samples collected. Small intestinal jejunum and muscles samples were collected and frozen in liquid nitrogen and additional jejunum samples placed in 10% formalin for latter analysis.

EXAMPLE 9

Fatty Acid Analysis

Lipids were extracted from piglet muscle and liver by the method of Lepage and Roy [J. Lipid Res., 27: 114-120 (1986), incorporated herein by reference] with minor modifications. Briefly, 0.5 grams of tissue was homogenized in 2.5 mL 4:1 methanol:hexane and then 200 µL of a 3.7 mmol heptadecanoic acid/L methanol solution added to each sample as an internal standard. Fatty acid methyl esters were analysed by gas chromatography on a Hewlett-Packard model 6890 (Hewlett-Packard, Palo Alto, Calif.) fitted with a Omegawax 320 (30 m×0.32 mm ID, 0.25 µm) capillary column (Sigma-Aldrich, St Louis, Mo. USA). Hydrogen was the carrier gas. The temperature program ranged from 80° C. to 250° C. with a temperature rise of 5° C./min. The injector and detector temperatures were 250° C. and 1 µL of sample was injected and run splitless. Fatty acids were identified by their retention times on the column as judged from appropriate standards.

Piglet Tissues Reflect Dietary Fatty Acid Profiles of Maternal Diet

Fatty acid profiles for the jejunum and longissimus muscle are presented in Tables 14 and 15. Feeding PFO throughout gestation and lactation resulted in significantly (P<0.05) higher n-3 PUFA contents in both the jejunum and muscle vs. the CONT/CONT regimen. This increase was achieved by both DHA and EPA in the jejunum, but muscle showed enrichment largely as DHA. Discontinuing the PFO diet at the onset of lactation caused a significant decrease in the DHA, EPA, and total n-3 contents in both tissues. However, feeding the PFO diet for the lactation period alone achieved similar enrichment as did feeding this n-3 source for the entire 150 days.

EXAMPLE 10

Ussing Chamber

Proximal jejunum samples, starting 40 cm from the stomach and consisting of a 20-30 cm segment of the jejunum, were removed and placed in chilled Krebs-Henseleit buffer (pH 7.4), which consisted of the following: 25 mM NaHCO3, 120 mM NaCl, 1 mM MgSO4, 6.3 mM KCl, 2 mM CaCl, 0.32 mM NaH2PO4. The tissue was aerated continuously until clamped in the Ussing chambers in the laboratory. The tunica muscularis was removed from two jejunal segments per pig, and mounted immediately in Ussing Chambers (DVC 1000 World Precision Instruments, New haven, CT USA). Each segment was bathed on its mucosal and serosal surfaces (opening area 1.0 cm2) with 8 mL Krebs solution and gassed with 95% O2-5% CO2 mixture. The voltage was clamped at 0 mV by an external current after correction for solution resistance. After a 30 minute period to allow the tissues to stabilize, they were challenged with 10 mM D-Glucose added to serosal buffer, and an equimolar concentration of mannitol added to the mucosal buffer. Additionally, jejunum samples from some CONT/CONT piglets were mounted, stabilized and treated (mucosal) with 0.1 mM DHA or 2.5 mM AICAR solubilised in 20 mM taurocholic acid. Glucose uptake was then assessed after 20 minutes, with the tissues challenged with 10 mM D-glucose as described earlier. The potential difference across the tissue was measured for 30 minutes after each challenge by open circuit conditions every 10 seconds due to a short-circuit current being delivered by a voltage clamp apparatus. The change in maximal current was recorded and the tissue conductance was calculated from the short-circuit current and potential difference using Ohm's law. This procedure was repeated on four different days with a pig from each dietary regimen to achieve a total of four pigs per treatment.

Glucose Transport

Figure 5:
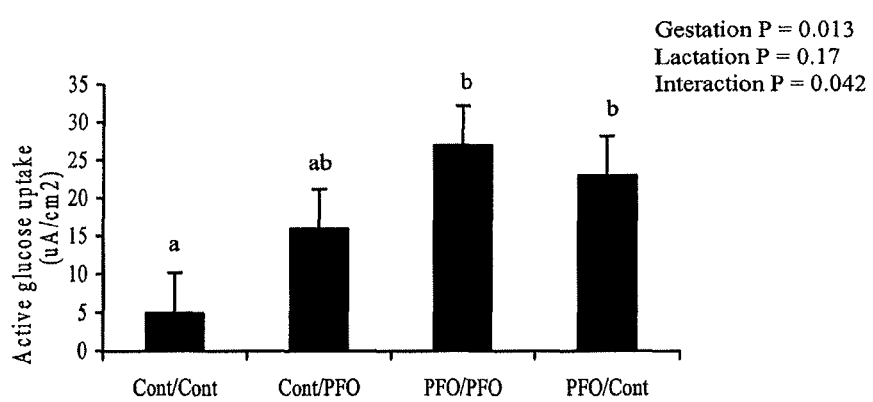
FIG. 5 shows ex vivo active glucose uptake by proximal jejunum of piglets at 21 days of age after deprivation of feed for 24 hours to simulate weaning stress. Dams were fed the control (Cont) and protected fish oil (PFO) dietary regimens during gestation and/or lactation (G/L). Data represent the means of 6 piglets per treatment. Means without a common letter are significantly different (P<0.05).

Changes in active glucose transport in the jejunum of piglets weaned from the dams fed the CONT or PFO diets were compared. As shown in FIG. 5, feeding PFO throughout gestation and lactation increased glucose uptake by 500% (5 vs 25 µA/cm$^2$, P<0.05), and providing the n-3 source in gestation alone improved glucose uptake by about 400%. In contrast, feeding PFO in lactation only precluded any significant enhancement in glucose uptake (15 vs 5 µA/cm$^2$, respectively, P=0.16).

EXAMPLE 11

Immunoblot Analysis of Glucose Transport Proteins in Total and Brush Border Membrane Preparations Fresh intact proximal jejunum was removed, washed with saline and placed on ice while approximately 4 g of mucosa were removed and transferred to cold 2 mM Tris-HCl buffer (pH 7.1) containing 50 mM mannitol and protease inhibitors (5 µM aprotinin, leupeptin, and pepstatin). The mucosa was then homogenized and PEG 4000 was added to a final concentration of 10% and stirred on ice for 15 minutes. The homogenate was then centrifuged for 15 minutes at 7,500×g and the resulting supernatant fraction centrifuged at 27,000×g for 60 minutes at 4° C. The pellet was washed in suspension buffer (10 mM Tris-HCl, pH 7.1, containing 300 mM mannitol and protease inhibitors 5 µM aprotinin, leupeptin, and pepstatin) and collected again by centrifugation for 5 minutes, 27,000×g at 4° C. The crude brush border membrane (BBM) pellet was suspended in 1 mL of suspension buffer. For preparation of total membranes, frozen jejunum sections (1 g) were and homogenized on ice in 700 µL Buffer A (50 mM Tris-HCl pH 7.5, 50 mM NaF, 5 mM sodium pyrophosphate, 1 mM EDTA, 1 mM DTT, 0.1 mM phenylmethylsulfonyl fluoride, 10% glycerol) containing 1% Triton X-100 and 5 µM aprotinin, leupeptin, and pepstatin. The homogenates were centrifuged at 6,000×g for 20 minutes at 4° C. to remove insoluble material. The protein concentrations of the total and BBM preparations were determined using BCA reagents (Pierce, Rockford, Ill., USA). Final total and brush border membrane preparations were frozen at −80° C. until assayed. The purity of the brush border membrane preparations as measured by alkaline phosphatase were not affected by treatment (data not shown).

The abundance of GLUT2 and SGLT1 protein in total and crude BBM was determined by western blot analysis. Briefly, membrane preparations containing 250 µg protein were immunoprecipitated at room temperature for 2 h using the Catch and Release v2.0 Reversible Immunoprecipitation System (Upstate Cell Signalling Solutions, Charlottesville, Va., USA). Both GLUT2 and SGLT1 were immunoprecipitated with 1:100 primary antibody (Chemicom International, Temecula, Calif. USA) dilutions. Immunoprecipitated proteins was separated by SDS-PAGE using a 12% resolving gel, transferred to a nitrocellulose membrane, and incubated with primary GLUT2 or SGLT1 antibody (1:1000 dilutions) overnight.

Expression of Glucose Transport Proteins in the Jejunum.

Figure 6:
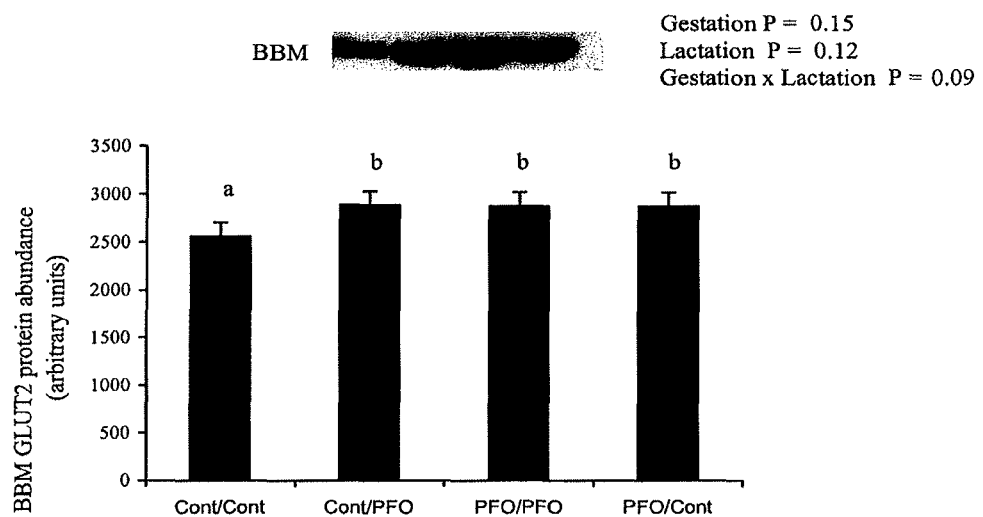
FIG. 6 shows an abundance of GLUT2 protein in the crude brush border membranes (BBM) (panel A) and total tissue preparations (panel B) from the proximal jejunum of piglets at 21 days of age after deprivation of feed for 24 hours to simulate weaning stress. Dams were fed the control (Cont) and protected fish oil (PFO) dietary regimens during gestation and/or lactation (G/L). Data represent the means SE of 6 piglets per treatment. Means without a common letter are significantly different (P<0.05).
Figure 6:
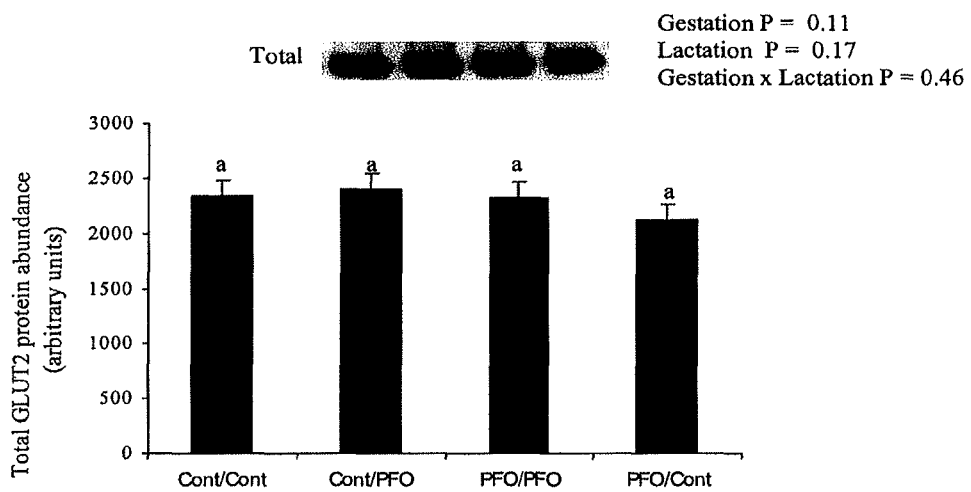

Immunoblots for GLUT2 abundance in the crude BBM preparations showed a small but significant (P<0.05) enrichment in the latter fraction obtained from piglets of dams consuming the PFO diets (FIG. 6, panel A), but there was no apparent change in abundance in total homogenates (FIG. 6, panel B). This result was not influenced by duration of the PFO regimen, nor was it specific for the gestation or lactation periods.

Figure 7:
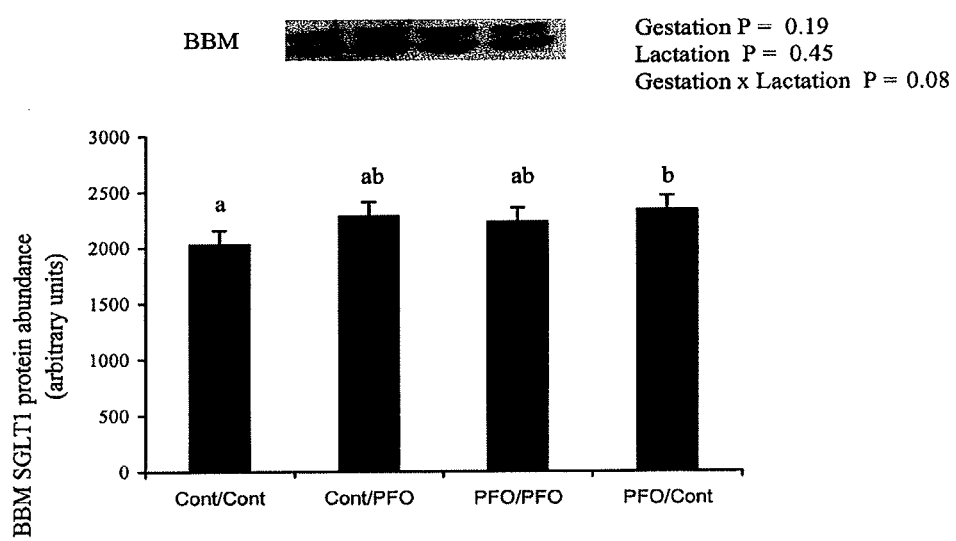
FIG. 7 shows an abundance of SGLT1 protein in the crude brush border membranes (BBM) (panel A) and total tissue preparations (panel B) from the proximal jejunum of piglets at 21 days of age after deprivation of feed for 24 hours to simulate weaning stress. Dams were fed the control (Cont) and protected fish oil (PFO) dietary regimens during gestation and(or) lactation (G/L). Data represent the means±SE of 6 piglets per treatment. Means without a common letter are significantly different (P<0.05), and the Cont/Cont and Cont/PFO differed at P<0.10.
Figure 7:
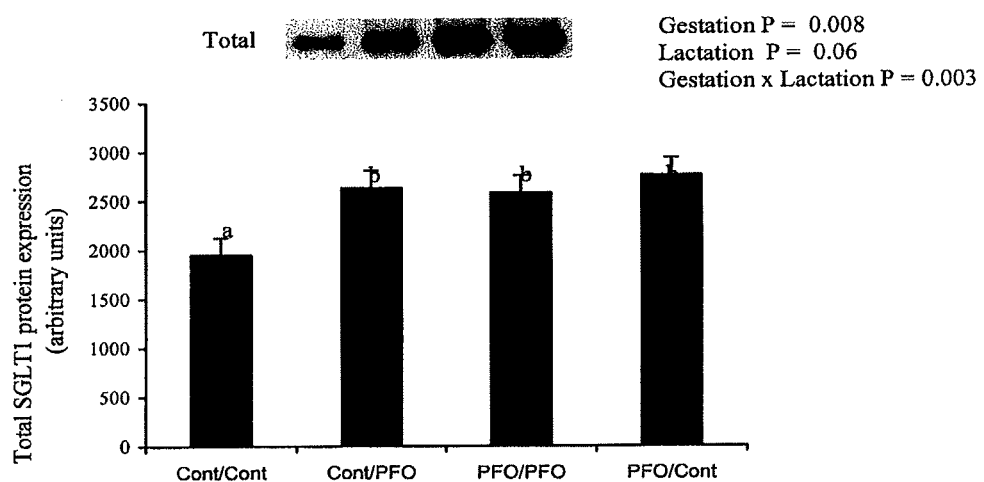

Similar immunoblots were performed for SGLT1. As seen in FIG. 7, panel A, the CONT/PFO dietary regimen tended to increased the abundance of the SGLT1 protein in the BBM preparations, but only the PFO/CONT regimen was significant (P<0.05). In contrast, feeding PFO in any dietary regimen increased (P<0.06) the abundance of SGLT1 protein in the total homogenate (FIG. 7, panel B).

EXAMPLE 12

Statistical Analyses

All data are expressed as means±SEM. The effects of dietary treatment regimen were determined by the PROC MIXED procedure is SAS (Version 9.1, SAS Institute, Cary, N.C.) and treatment differences were established using least significant differences procedure when protected by a significant F-value. The effect of gestation, lactation or gestation and lactation n-3 PUFA feeding was assessed in the model. Litter/piglet was considered the experimental unit and experimental replicate or day of harvest was considered a random effect. Differences were deemed significant at P<0.05, and tendencies are noted at P<0.10.

EXAMPLE 13

Experimental Design

A total of four experimental dietary treatments were employed. The dietary treatments consisted of 1) basal corn/soybean meal (no added fat, control), or the basal diet supplemented with either 2) protected fish oil (Fertilium™ or PFO), 3) alDHA, and 4) extruded Coconut fat (Coco) (Table 1). The fatty acid profiles of the dietary ingredients used to provide the fatty acids to the various diets are shown in Table 7. The fatty acid composition of all diets used in this experiment were balanced of the total crude fat percentage of the diets, with the DHA percentage of the DHA diets matched to that of the DHA percentage calculated in the Fertilium™ diet. Sows were fed a gestation and lactation diet (Tables 1, 2, and 8) continuously starting approximately 35-d prior to breeding. Nursery pigs were introduced to starter diets and taken through a four phase dietary regime (Table 9). Upon exit of the nurseries, pigs were phase fed diets (Table 10) containing one of the four experimental treatments.

EXAMPLE 14

Animals

Sows and Piglets.

Sows were housed in fully enclosed gestation and farrowing rooms which were climate controlled. Two hundred forty AusGene genetic sows were allocated to one of four experimental treatments approximately 35-d prior to breeding. Dry and lactating sows had free access to water at all times and were fed twice daily. Experimental litters were formed by standardizing litters within treatment. Within treatment, all the piglets on that farrowing day were pooled and then individually weighed as they were cross-fostered back onto sows of the same treatment. Experimental sow had approximately 10-11 piglets. Individual piglet weights, total number and sex data was recorded for each experimental litter and the piglets were tattoo and ear notched for treatment, litter and piglet number.

Approximately 2200 piglets were allocated to weaner treatments (Table 9) and weaned to three barns at the production farm the following day. Piglets from sows fed trt 2-4 were evenly split and maintained on either their sow treatment or switch to Coco (if on PUFA diets) or PFO if on Coco diet. Therefore four treatments went to seven consisting of the following: control stayed as the control; PFO, PFO/Coco or PFO/PFO; DHA, DHA/Coco or DHA/DHA and Coco, Coco/PFO or Coco/Coco. Weaned pens aimed to have 24 pigs per pen, equal sex, weight and covariant distributions. Nursery pens were randomly blocked within barns and a total of nine treatment reps were achieved.

Nursery.

The nursery rooms at the production farm were also thermostatically controlled at the initial temperature of 30° C. and the temperature was decreased weekly to a target temperature of 25° C. Piglets had free access to water and were fed ad libitum with a starter pellet diet for two weeks before changing to a ground diet. At the end of week 13, pigs, keeping the nursery pens in tacked, were transferred to finisher penned within the same barn.

Grower-Finisher.

Within the finisher barns, pigs had free access to water and were again feed ad libitum a ground feed containing either control, PFO, DHA or Coco treatment (Table 10).

Overall Growth Performance.

Feed conversion efficiency tended to be improved by up to 2.5% ($P<0.10$, Table 11) in all PFO or DHA treatments, except for when pigs which had in utero Coco exposure, compared to the control treatment. Exposure of piglets to EPA and DHA in utero and in the sow's milk improved feed conversion in the offspring ($P<0.10$).

Increase in Piglet Pre-Weaning Growth Rate and Reduced Pre-Weaning Mortality when Sows were Fed n-3 PUFA During Gestation and Lactation.

Sows were fed corn/sbm diets supplemented with protected n-3 PUFA from Fertilium™ to provide 0.022% DHA and EPA in the final sow feed (Tables 12 and 13). Diets were fed to sows for approximately 35-days prior to breeding and for the entire subsequent gestation and lactation period. Litters were all standardized to the same number of piglets. Number of pigs and litter weight was collected 14-days post farrowing to determine dietary impact on piglet pre-weaning growth rate and mortality rate. The Fertilium™ diet increased the number of pigs weaned and the pig weaning weight (Tables 12 and 13).

EXAMPLE 15

Statistical Analyses

All data was analyzed by PROC MIXED procedure is SAS (Version 9.1, SAS Institute, Cary, N.C.). In the lactation experiments, sow was considered the experimental unit and blocked on week and farrowing room. For nursery and grower-finisher experimental data, pen was the experimental unit and was blocked on treatment and by the nine reps generated at weaning.

EXAMPLE 16

Nutrient Transport in Chicks

Nine S1 Leghorn layer hens were housed in individual pens in one section of an environmentally controlled facility. Hens were fed diets differing in n-3 polyunsaturated fatty acid (PUFA) and docosahexaenoic acid (DHA) content, and formulated to meet NRC poultry requirements (National Research Council. 1994. Nutrient requirements of poultry. $9^{th}$ Ed. NRC, Washington D.C.). The three dietary treatments were fed to evaluate the impact of maternal n-3 PUFA and DHA intake on offspring intestinal nutrient uptake. Treatments included; 1) (CON) Diet supplemented with soybean oil at a dietary inclusion rate of 2.7%; 2) (PFO) Diet supplemented with protected fish oil from GROMEGA 365™ (JBS United, Sheridan, Ind.) at 13.56% of the diet to provide a non-algal source of DHA; or 3) (alDHA) Diet supplemented with DHA from *Schizochytrium* algae at 1.13% of the diet (Table 1). Additionally, the delivery of DHA from protected fish oil and algae was formulated to be equal for the PFO and alDHA treatments (Table 2). Diets were formulated based on an estimated daily feed intake of 115 g/hen/d.

TABLE 1

Experimental diets[a]

| Ingredient, % | Control | alDHA[a] | PFO[b] |
|---|---|---|---|
| Corn | 62.00 | 65.48 | 53.63 |
| Soybean meal | 24.96 | 23.03 | 22.43 |
| Limestone | 7.75 | 7.75 | 7.75 |
| Soybean Oil | 2.70 | 0.00 | 0.00 |
| alDHA[a] | 0.00 | 1.13 | 0.00 |
| PFO[b] | 0.00 | 0.00 | 13.56 |
| Dicalcium phosphate | 1.42 | 1.43 | 1.46 |
| Vitamin premix | 0.50 | 0.50 | 0.50 |
| Salt | 0.40 | 0.40 | 0.40 |
| DL-Methionine | 0.11 | 0.13 | 0.12 |
| Mineral premix | 0.10 | 0.10 | 0.10 |
| Selenium premix | 0.05 | 0.05 | 0.05 |

[a]alDHA = Sehizochytrium algae
[b]PFO = protected fish oil

TABLE 2

Formulated eicosapentaenoic acid (EPA) and docosahexaenoic acid (DHA) content of experimental diets and calculated daily intake (g/d)

| | Control | alDHA[a] | PFO[b] |
|---|---|---|---|
| Inclusion rate of supplement, % | 0.00 | 1.13 | 13.56 |
| EPA content of supplement, % | 0.00 | 0.99 | 2.61 |
| DHA content of supplement, % | 0.00 | 20.94 | 1.73 |
| EPA supplemented to hen diet, % | 0.00 | 0.01 | 0.35 |
| DHA supplemented to hen diet, % | 0.00 | 0.24 | 0.24 |
| Estimated daily intake, g/d | 115 | 115 | 115 |
| Estimated EPA intake, g/d | 0.00 | 0.01 | 0.41 |
| Estimated DHA intake, g/d | 0.00 | 0.27 | 0.27 |

[a]alDHA =Schizochytrium algae
[b]PFO =protected fish oil

EXAMPLE 17

Animal Protocol

Nutrient Transport in Chicks

Hens were fed the experimental diets for 21 days prior to the collection of approximately 10 fertile eggs from each of 3 hens/trt for hatching (30 eggs set for hatch per treatment). Post hatch, approximately five, 3-day old chicks from each hen were sacrificed for analysis of intestinal glucose and glutamine uptake (15 chicks/trt). Fertile eggs were incubated at 37.5° C. and 60.4% relative humidity in a commercial egg incubator with automatic egg turning (Jamesway, Model #252), and on day 19 the eggs were transferred to a hatching basket and hatched in the incubator. At hatching, chicks were placed in pre-warmed battery cages and provided water and a common chick starter diet. At approximately 72 hours post-hatch, chicks were euthanized by $CO_2$ asphyxiation and intestinal jejunum segments were harvested for evaluation of intestinal nutrient absorption.

EXAMPLE 18

Ussing Chamber Protocol

Nutrient Transport in Chicks

Proximal jejunum samples between the bile duct and the yolk-sac were removed and placed in chilled Krebs-Henseleit buffer (consisting in mmol/L: 25 NaHCO$_3$, 120 NaCl, 1 MgSO$_4$, 6.3 KCl, 2 CaCl, 0.32 NaH$_2$PO$_4$; pH 7.4) for transport back to the laboratory (<40 min) under constant aeration until clamped in the Ussing chambers. Two jejunal segments per chick were immediately mounted in Ussing Chambers (DVC 4000 World Precision Instruments, New haven, CT USA). Each segment was bathed on its mucosal and serosal surfaces (opening area 1.0 cm$^2$) with 3 mL Krebs solution and gassed with 95% O$_2$-5% CO$_2$ mixture. The intestinal segments were voltage clamped at zero mV by an external current after correction for solution resistance. After a short-circuit current was established and stabilized (5 to 10 min), basal short-circuit current measurements were taken using MP100A software (BioPac Systems Inc., Santa Barbara, Calif.). The software allowed real-time measurements of current and thus changes in current were constantly monitored. After the tissue was stabilized, they were challenged independently with 10 mmol/L D-Glucose and 10 mmol/L L-glutamine which was added to serosal buffer, with equimolar (10 mmol/L) mannitol added on the mucosal side. The change in maximal current was recorded and this was repeated on four different days with a total of ten chicks per treatment.

EXAMPLE 19

Fatty Acid Modulation of Nutrient Transport in Chicks

Figure 8:
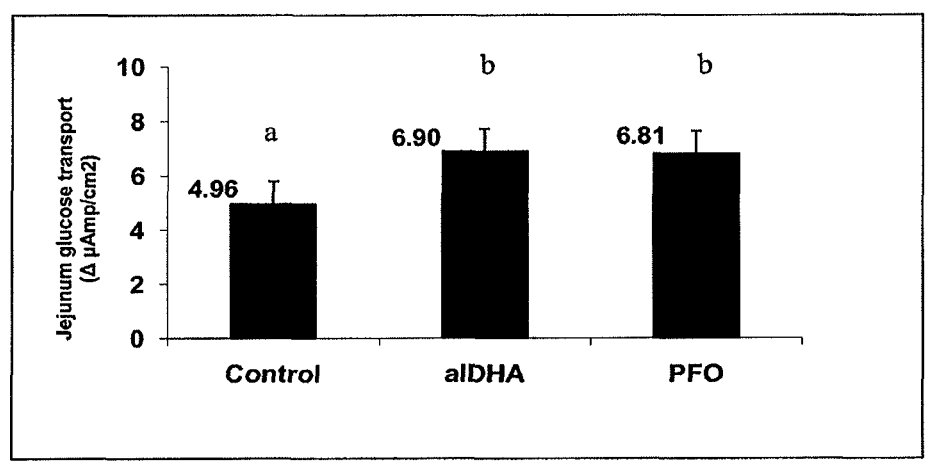
FIG. 8 shows jejunum glucose uptake in chicks. Values are least squares means±SEM (n=10/treatment). Different letters represent significant differences at P<0.05.
Figure 9:
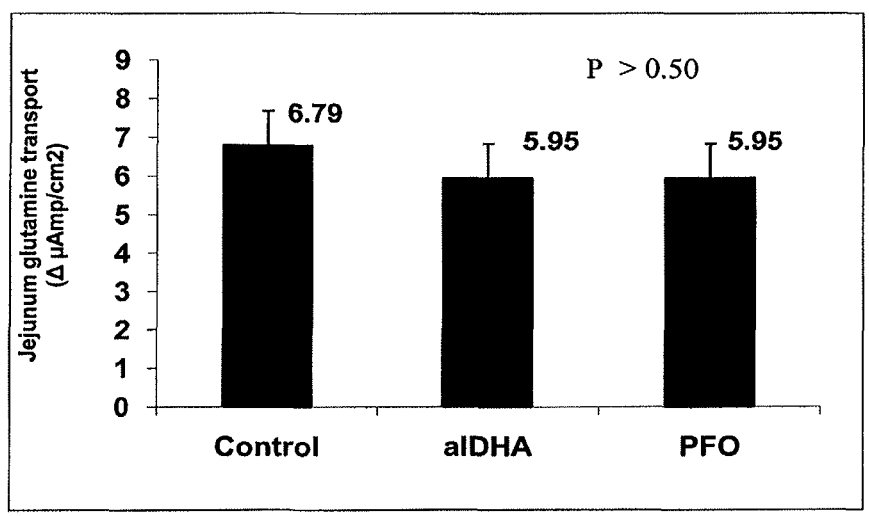
FIG. 9 shows jejunum glutamine uptake in chicks. Values are least squares means±SEM (n=10/treatment).

FIG. 8 shows jejunum glucose uptake in three day-old chicks from hens fed a diet enriched with DHA from *Schizochytrium* algae (alDHA) or protected fish oil (PFO). Intestinal glucose transport (10 mM) was assessed by modified Ussing chamber technique as described above. FIG. 9 shows jejunum glutamine uptake in three day-old chicks from hens fed a diet enriched with DHA from *Schizochytrium* algae (alDHA) or protected fish oil (PFO). Intestinal glucose transport (10 mM) was assessed by modified Ussing chamber technique.

Chicks hatched from hens supplemented n-3 PUFA and DHA from either algal (alDHA) and non-algal (PFO) sources displayed significantly increased jejunal glucose uptake compared to chicks hatched from hens not supplemented with n-3 PUPA or DHA ($P<0.05$) (FIG. 8). Active glucose uptake in alDHA and PFO treatments were 41% and 37% greater than in chicks fed the control diet, respectively. There was no difference in glucose uptake between alDHA or PFO ($P>0.50$) (FIG. 8). There was no difference among treatments for glutamine uptake ($P>0.10$) (FIG. 9).

EXAMPLE 20
EXEMPLARY PFO FORMULA

The following are exemplary formulas for a non-algal composition comprising omega-3 fatty acids or esters thereof that may be added to the feed compositions as herein described.

| Ingredient | % of Product |
|---|---|
| Extruded GroMega Formula #1: | |
| Wheat Flour | 65.45 |
| Menhaden Oil | 20.00 |
| Alfalfa Meal | 8.80 |
| Dry Molases | 5.60 |
| Vitamin Pack | 0.15 |
| Swine 10-20 lbs/ton complete feed | |
| Ratio DHA:EPA .75-1:1 | |
| Extruded GroMega Formula #2: | |
| Menhaden Oil | 60 |
| Starch Carrier | 40 |
| Total | 100 |
| Swine 5-10 lbs/ton of complete feed | |
| Ratio DHA:EPA .75-1:1 | |

TABLE 1

Sow gestation and lactation diets (as fed basis)

| | Gestation | | | | Lactation | | | |
|---|---|---|---|---|---|---|---|---|
| | CON | PFO | alDHA | Coconut | CONT | PFO | alDHA | Coconut |
| Ingredient, % | | | | | | | | |
| Corn | 75.69 | 75.69 | 75.69 | 75.69 | 64.96 | 64.9 | 64.96 | 64.96 |
| Soybean Meal, 48% | 18.66 | 18.66 | 18.66 | 18.66 | 27.74 | 27.7 | 27.74 | 27.74 |
| Premix | 4.65[1] | 4.65[1] | 4.65[1] | 4.65[1] | 6.30[2] | 6.30[2] | 6.30[2] | 6.30[2] |
| Corn Starch | 1.00 | — | 0.86 | — | 1.00 | — | 0.86 | — |
| Protected fish oil (PFO)[3] | — | 1.00 | — | — | — | 1.00 | — | — |
| Algal DHA (alDHA) | — | — | 0.14 | — | — | — | 0.14 | — |
| Dry coconut fat | — | — | — | 1.00 | — | — | — | 1.00 |
| Total | 100 | 100 | 100 | 100 | 100 | 100 | 100 | 100 |
| Calculated nutrient content, % | | | | | | | | |
| Crude fat | 3.56 | 3.78 | 3.56 | 4.36 | 3.45 | 3.66 | 3.45 | 4.25 |
| Crude protein | 15.17 | 15.26 | 15.17 | 15.21 | 19.09 | 19.1 | 19.09 | 19.13 |
| Starch | 48.86 | 48.35 | 48.75 | 47.87 | 42.75 | 42.2 | 42.60 | 41.77 |
| Metabolizable energy, MJ/kg | 13.68 | 13.68 | 13.72 | 13.85 | 13.56 | 13.6 | 13.51 | 13.72 |
| Lysine | 0.75 | 0.75 | 0.75 | 0.75 | 1.10 | 1.10 | 1.10 | 1.10 |

TABLE 1-continued

Sow gestation and lactation diets (as fed basis)

| | Gestation | | | | Lactation | | | |
|---|---|---|---|---|---|---|---|---|
| | CON | PFO | alDHA | Coconut | CONT | PFO | alDHA | Coconut |
| Phosphorus | 0.77 | 0.77 | 0.77 | 0.77 | 0.81 | 0.81 | 0.81 | 0.81 |
| Calcium | 0.88 | 0.88 | 0.88 | 0.88 | 0.91 | 0.91 | 0.91 | 0.91 |

[1]The premix provided per kg of diet: 662 mg of choline as choline chloride; 3.35 mg of retinyl acetate; 0.06 mg of cholecalciferol; 66 mg of vitamin E as alphatocopherol acetate; 1.4 mg of vitamin K as menadione dimethypyrimidinol bisulfate; 0.44 mg of biotin; 44 mg of niacin; 24 mg of pantothenic acid; 7 mg of riboflavin; 0.03 mg of vitamin B-12; 1.61 mg of folic acid; 0.25 mg of pyridoxine as pyridoxine HCl; 0.48 mg of thiamine; P, 0.43% as monocalcium phosphate; Ca, 0.80% as calcium carbonate; Na, 0.18% as sodium chloride; K, 0.25% as potassium chloride; Mg, 0.02% magnesium Cu, 10 mg as copper sulfate; Fe, 125 mg as iron sulfate; I, 1.26 as potassium iodate; Mn, 60 mg as manganese sulfate; Se, 0.3 mg as sodium selenite; Zn, 125 mg as zinc sulfate.
[2]Premix provided per kg of diet: 662 mg of choline as choline chloride; 3.35 mg of retinyl acetate; 0.06 mg of cholecalciferol; 66 of vitamin E as alphatocopherol acetate; 1.4 mg of vitamin K as menadione dimethypyrimidinol bisulfate; 0.44 mg of biotin; 44mg niacin; 24 mg of pantothenic acid; 7 mg of riboflavin; 0.03 mg of vitamin B-12; 1.59 mg of folic acid; 0.25 mg of pyridoxine as pyridoxine HCl; 0.48 mg of thiamine; P, 0.43% as monocalcium phosphate; Ca, 1.0% as calcium carbonate; Na, 0.21% as sodium chloride; K, 0.37% as potassium chloride; Mg, 0.06% magnesium; Cu, 10 mg as copper sulfate; Fe, 136 mg as iron sulfate; I, 1.26 as potassium iodate; Mn, 60 mg as manganese sulfate; Se, 0.3 mg as sodium selenite; Zn, 125 mg as zinc sulfate; and 0.08% Lys as lysine HCL.
[3]Protected fish oil was supplied by JBS United, Inc.

TABLE 2

Sow lactation diet fatty acid composition

| | Diet | | | |
|---|---|---|---|---|
| | CONT | PFO | alDHA | COCO |
| | (g/100 g total fatty acids) | | | |
| 6:0 | 0.00 | 0.00 | 0.00 | 0.06 |
| 8:0 | 0.00 | 0.00 | 0.00 | 1.44 |
| 10:0 | 0.00 | 0.00 | 0.00 | 1.11 |
| 12:0 | 0.00 | 1.37 | 1.38 | 8.97 |
| 14:0 | 0.00 | 0.47 | 0.28 | 3.82 |
| 16:0 | 15.53 | 15.56 | 15.22 | 14.53 |
| 16:1 | 0.00 | 0.67 | 0.00 | 0.00 |
| 18:0 | 3.18 | 3.20 | 2.95 | 3.09 |
| 18:1 | 23.63 | 21.55 | 23.19 | 19.19 |
| 18:2(n-6) | 54.07 | 52.36 | 52.74 | 44.53 |
| 18:3(n-3) | 3.02 | 3.05 | 2.88 | 2.69 |
| 20:0 | 0.44 | 0.41 | 0.44 | 0.36 |
| 20:1 | 0.00 | 0.27 | 0.00 | 0.00 |
| 20:3(n-6) | 0.00 | 0.00 | 0.00 | 0.00 |
| 20:5(n-3) | 0.00 | 0.58 | 0.00 | 0.00 |
| 22:5(n-3) | 0.00 | 0.00 | 0.00 | 0.00 |
| 22:6(n-3) | 0.00 | 0.51 | 0.80 | 0.00 |
| Other | 0.12 | 0.00 | 0.12 | 0.20 |
| Saturated | 19.27 | 21.51 | 21.20 | 33.58 |
| Total (n-3) | 3.02 | 4.14 | 3.68 | 2.69 |
| Total (n-6) | 54.07 | 52.36 | 52.74 | 44.53 |
| (n-6)/(n-3) | 17.90 | 12.6 | 14.3 | 16.5 |

TABLE 3

Sow milk fatty acid profile following gestation and lactation feeding of fatty acid modified diets[1,2]

| | Diet | | | | Pooled |
|---|---|---|---|---|---|
| | CONT | PFO | alDHA | COCO | SEM |
| | (g/100 g total fatty acids) | | | | |
| 10:0 | 0.24 | 0.17 | 0.18 | 0.28 | 0.059 |
| 12:0 | 0.27[a] | 0.20[a] | 0.23[a] | 1.30[b] | 0.154 |
| 14:0 | 3.61 | 2.68 | 3.14 | 4.28 | 0.586 |
| 16:0 | 33.91 | 27.59 | 28.59 | 34.47 | 3.091 |
| 16:1 | 10.51 | 7.84 | 8.83 | 10.87 | 2.55 |
| 18:0 | 5.08 | 5.55 | 5.49 | 4.73 | 0.305 |
| 18:1 | 29.89 | 39.22 | 36.69 | 28.78 | 4.733 |
| 18:2(n-6) | 13.39 | 13.08 | 13.18 | 12.26 | 1.640 |
| 18:3(n-3) | 0.61 | 0.57 | 0.56 | 0.55 | 0.053 |
| 20:0 | 0.09 | 0.06 | 0.12 | 0.04 | 0.061 |
| 20:1 | 0.22 | 0.42 | 0.36 | 0.25 | 0.144 |
| 20:2 | 0.25 | 0.42 | 0.43 | 0.30 | 0.101 |
| 20:3(n-6) | 0.34 | 0.07 | 0.10 | 0.00 | 0.203 |
| 20:4(n-6) | 0.50 | 0.67 | 0.71 | 0.82 | 0.208 |
| 20:5(n-3) | 0.00 | 0.07 | 0.00 | 0.00 | 0.040 |
| 22:5(n-3) | 0.00[a] | 0.27[b] | 0.12[ab] | 0.00[a] | 0.069 |
| 22:6(n-3) | 0.00[a] | 0.24[b] | 0.29[b] | 0.00[a] | 0.035 |
| Other | 1.07 | 0.88 | 0.99 | 1.06 | 0.149 |
| Saturated | 43.31[bc] | 36.25[a] | 37.75[ab] | 45.11[c] | 3.512 |
| Total (n-3) | 0.61[a] | 1.16[b] | 0.97[b] | 0.55[a] | 0.122 |
| Total (n-6) | 14.72 | 14.41 | 14.60 | 13.68 | 1.926 |
| (n-6)/(n-3) | 24.1[b] | 12.52[a] | 15.4[a] | 24.9[b] | 1.611 |

[1]Means of milk samples collected from 4 sows per treatment.
[2]Within a row, means with superscripts without a common letter differ, $P < 0.05$.

TABLE 4

Piglet fatty acid composition of longissimus dorsi muscle and proximal jejunum samples taken at weaning[1,2]

| | Small intestine | | | | | Muscle | | | | |
|---|---|---|---|---|---|---|---|---|---|---|
| Fatty acid | CONT | PFO | alDHA | COCO | Pooled | CONT | PFO | alDHA | COCO | Pooled |
| | (g/100 g total fatty acid) | | | | | | | | | |
| 10:0 | 0.00 | 0.00 | 0.00 | 0.00 | — | 0.00 | 0.00 | 0.00 | 0.00 | — |
| 12:0 | 0.00 | 0.00 | 0.00 | 0.00 | — | 0.00 | 0.03 | 0.00 | 0.06 | 0.043 |
| 14:0 | 0.13[a] | 0.28[ab] | 0.36[b] | 0.46[b] | 0.067 | 1.93 | 1.78 | 2.13 | 2.28 | 0.355 |
| 16:0 | 20.84 | 20.95 | 23.15 | 23.15 | 1.711 | 33.51 | 29.62[ab] | 28.86[b] | 31.74[ac] | 0.870 |
| 16:1 | 1.96 | 1.43 | 1.80 | 2.35 | 0.297 | 9.07 | 6.24 | 7.81 | 8.66 | 1.570 |
| 18:0 | 22.32 | 22.22 | 23.34 | 21.64 | 0.867 | 10.23 | 10.25 | 9.26 | 10.71 | 1.270 |
| 18:1 | 13.20 | 14.10 | 11.63 | 13.55 | 2.088 | 25.02 | 27.54 | 31.86 | 23.54 | 3.037 |
| 18:2(n-6) | 21.78 | 20.78 | 21.60 | 21.18 | 1.501 | 15.69 | 16.47 | 14.07 | 16.58 | 1.751 |
| 18:3(n-3) | 0.46 | 0.13 | 0.07 | 0.21 | 0.202 | 0.25 | 0.21 | 0.42 | 0.24 | 0.152 |
| 20:0 | 0.55 | 0.65 | 0.51 | 0.47 | 0.193 | 0.00 | 0.00 | 0.00 | 0.00 | — |
| 20:1 | 0.00 | 0.05 | 0.04 | 0.00 | 0.037 | 0.15 | 0.25 | 0.48 | 0.15 | 0.121 |

TABLE 4-continued

Piglet fatty acid composition of longissimus dorsi muscle and proximal jejunum samples taken at weaning[1, 2]

| Fatty acid | Small intestine | | | | | Muscle | | | | |
|---|---|---|---|---|---|---|---|---|---|---|
| | CONT | PFO | alDHA | COCO | Pooled | CONT | PFO | alDHA | COCO | Pooled |
| 20:2 | 0.30 | 0.38 | 0.39 | 0.27 | 0.100 | 0.20 | 0.37 | 0.51 | 0.19 | 0.144 |
| 20:3(n-6) | 0.67 | 0.69 | 0.71 | 0.66 | 0.052 | 0.43 | 0.34 | 0.38 | 0.48 | 0.130 |
| 20:4(n-6) | 12.92 | 11.72 | 11.60 | 12.25 | 0.918 | 2.67 | 4.48 | 2.88 | 4.36 | 1.121 |
| 20:5(n-3) | 0.00[a] | 0.47b | 0.18[a] | 0.10[a] | 0.121 | 0.00 | 0.03 | 0.00 | 0.00 | 0.018 |
| 22:4 | 1.59 | 1.15 | 1.06 | 1.67 | 0.207 | 0.49 | 0.64 | 0.46 | 0.81 | 0.199 |
| 22:5(n-3) | 0.92[ab] | 1.06[ab] | 0.67[a] | 0.78[ab] | 0.124 | 0.23[a] | 0.82[b] | 0.31[ab] | 0.07[a] | 0.178 |
| 22:6(n-3) | 0.90[a] | 2.54b | 2.34[b] | 0.65[a] | 0.338 | 0.00[a] | 0.81[b] | 0.54[b] | 0.00[a] | 0.132 |
| Other | 1.47 | 1.43 | 0.57 | 0.63 | 0.779 | 0.15 | 0.10 | 0.05 | 0.14 | 0.116 |
| Saturated | 45.26 | 45.50 | 47.84 | 46.14 | | 45.66[c] | 41.73[ab] | 40.25[a] | 44.78[bc] | 1.162 |
| (n-3) | 2.28 | 4.19 | 3.26 | 1.74 | | 0.48[a] | 1.87b | 1.27[b] | 0.31a | 0.244 |
| (n-6) | 35.41 | 33.21 | 33.99 | 34.17 | | 18.36 | 20.98 | 16.95 | 20.94 | 2.661 |
| (n-6)/(n-3) | 15.56 | 7.93 | 10.43 | 19.61 | | 28.11[a] | 11.20[b] | 13.40[b] | 28.07[a] | 4.590 |

[1]Means of four piglets per treatment.
[2]Within a tissue and row, means with superscripts without a common letter differ, P < 0.05.

TABLE 5

Gestation and lactation diets (as fed basis)

| | Gestation | | Lactation | |
|---|---|---|---|---|
| Ingredient, % | Control | PFO | Control | PFO |
| Corn | 75.69 | 75.69 | 64.96 | 64.96 |
| Soybean Meal, 48% | 18.66 | 18.66 | 27.74 | 27.74 |
| Vitamin/mineral/phytase premix | 4.65 | 4.65 | 6.30 | 6.30 |
| Corn Starch | 1.00 | — | 1.00 | — |
| Protected fish oil (PFO)[a] | — | 1.00 | — | 1.00 |
| Total | 100 | 100 | 100 | 100 |
| Calculated nutrient content, % | | | | |
| Crude fat | 3.56 | 3.78 | 3.45 | 3.66 |
| Crude protein | 15.17 | 15.26 | 19.09 | 19.18 |
| Lysine | 0.75 | 0.75 | 1.10 | 1.10 |
| Phosphorus | 0.77 | 0.77 | 0.81 | 0.81 |
| Calcium | 0.88 | 0.88 | 0.91 | 0.91 |
| EPA[b] | — | 0.007 | — | 0.007 |
| DHA[b] | — | 0.007 | — | 0.007 |
| 12:0, 14:0 and 16:0[b] | — | 0.013 | — | 0.013 |
| Total n-6 fatty acids | 1.58 | 1.58 | 1.43 | 1.43 |
| Total n-3 fatty acids | 0.06 | 0.13 | 0.07 | 0.14 |
| n-6:n-3 fatty acid ratio | 26.70 | 12.04 | 20.51 | 10.11 |

[a]Protected fish oil was supplied by JBS United, Inc.
[b]Calculated percentage of total fat in diet

TABLE 7

Diet additive ingredient fatty acid analysis profile.
Fatty acids presented as a percentage of total fatty acids.*

| | Dietary ingredient* | | |
|---|---|---|---|
| Fatty Acid | FERTILIUM ™ | aLDHA | Coconut |
| C10:0 | 0.258 | 0.098 | 6.702 |
| C12:0 (lauric) | 0.117 | 0.327 | 51.754 |
| C14:0 (myristic) | 8.662 | 9.117 | 19.393 |
| C16:0 (palmitic) | 18.009 | 23.127 | 9.625 |
| C16:1n7 | 11.190 | 0.048 | 0.029 |
| C18:0 (stearic) | 3.031 | 0.545 | 3.010 |
| C18:1n9 | 3.067 | 0.077 | 0.084 |
| C18:1n7 | 0.118 | 0.132 | 6.816 |
| C18:2n6 | 4.382 | 0.031 | 2.266 |
| C18:3n6 | 0.270 | 0.240 | |
| C18:3n3 (α-linolenic) | 1.476 | 0.097 | 0.090 |
| C20:0 | 0.182 | 0.167 | 0.091 |
| C20:1n9 | 1.419 | | 0.046 |
| C20:3n6 | 0.184 | 0.409 | |
| C20:4n6 (arachidonic) | 0.622 | 2.410 | |
| C20:3 | 0.242 | 0.237 | |
| C20:5n3 (EPA) | 12.806 | 1.656 | |
| C22:0 | 0.134 | 0.075 | 0.024 |
| C22:4n6 | 0.111 | 0.085 | |
| C22:5n6 | 0.343 | 15.736 | |
| C22:5n3 (DPA) | 2.185 | 0.405 | 0.034 |
| C24:0 | 0.268 | | |

TABLE 6

Preweaning mortality of litters reared by sows fed protected fish oil (PFO) in lactation
only (control/PFO), gestation only (PFO/Control), or both (PFO/PFO).

| | Treatment (gestation/lactation)* | | | | | Significance | | |
|---|---|---|---|---|---|---|---|---|
| | Control/Control[a] | Control/PFO[b] | PFO/PFO[c] | PFO/Control[d] | SEM | Gestation | Lactation | Interaction |
| Litter number | 11.3 | 10.9 | 11.0 | 11.0 | 0.26 | 0.97 | 0.41 | 0.42 |
| Wean number | 9.1 | 9.3 | 9.5 | 9.9 | 0.49 | 0.057 | 0.76 | 0.26 |
| Mortality %) | 14.9 | 9.1 | 11.0 | 7.3 | 2.55 | 0.14 | 038 | 0.016 |

*Sow number: superscripts a = 19, b = 16, c = 22 and d = 21 sows
$Sum of the born alive and stillborn

TABLE 7-continued

Diet additive ingredient fatty acid analysis profile.
Fatty acids presented as a percentage of total fatty acids.*

| Fatty Acid | Dietary ingredient* | | |
|---|---|---|---|
| | FERTILIUM ™ | aLDHA | Coconut |
| C22:6n3 (DHA) | 12.213 | 40.940 | — |
| Total n3 fatty acids | 28.680 | 43.100 | 0.124 |
| Total n6 fatty acids | 5.913 | 18.911 | 2.266 |
| Total saturated fatty acids | 30.527 | 33.381 | 87.565 |
| n6:n3 ratio | 0.21 | 0.44 | 21.25 |

TABLE 8

Experimental diets denoting the calculated balance of added fatty acids during sow gestation and lactation. Calculations based of the total crude fat percentage and DHA in both PUFA diets match to the content in the Fertilium diet.

| | Treatment | | | |
|---|---|---|---|---|
| | Control | FERTILIUM ™ | aLDHA | Coconut |
| Gestation diet | | | | |
| Crude fat (%) | 3.56 | 3.76 | 3.62 | 4.36 |
| EPA, as % of fat in diet | — | 0.007 | 0.0005 | — |
| DHA, as % of fat in diet | — | 0.007 | 0.007 | — |
| 12:0, 14:0, and 16:0 as % of | — | 0.013 | 0.006 | 0.134 |
| Total test fat in diet (%) | 0.000 | 0.266 | 0.037 | 0.229 |
| Lactation diet | | | | |
| Crude fat (%) | 3.45 | 3.66 | 3.52 | 4.25 |
| EPA, as % of fat in diet | — | 0.007 | 0.0005 | — |
| DHA, as % of fat in diet | — | 0.007 | 0.008 | — |
| 12:0, 14:0, and 16:0 as % of | — | 0.013 | 0.006 | 0.144 |
| Total test fat in diet (%) | 0.000 | 0.272 | 0.038 | 0.236 |

TABLE 9

The approximate calculated fatty acid balance of the nursery phase diets. Added fatty acids present were based on the total crude fat percentage and the DHA content match for both PUFA treatments to that in the Fertilium.

| | Treatment | | | |
|---|---|---|---|---|
| | Control | FERTILIUM ™ | aLDHA | Coconut |
| Phase 1 | | | | |
| Crude fat (%) | 8.41 | 8.89 | 8.56 | 10.76 |
| EPA, as % of fat in diet | — | 0.007 | 0.0005 | — |
| DHA, as % of fat in diet | — | 0.007 | 0.008 | — |
| 12:0, 14:0, and 16:0 as % | — | 0.013 | 0.006 | 0.139 |
| Total test fat in diet (%) | 0.000 | 0.272 | 0.039 | 0.235 |
| Phase 2 | | | | |
| Crude fat (%) | 3.46 | 3.64 | 3.52 | 4.22 |
| EPA, as % of fat in diet | — | 0.007 | 0.0005 | — |
| DHA, as % of fat in diet | — | 0.007 | 0.008 | — |
| 12:0, 14:0, and 16:0 as % | — | 0.013 | 0.006 | 0.139 |
| Total test fat in diet (%) | 0.000 | 0.272 | 0.038 | 0.236 |
| Phase 3 | | | | |
| Crude fat (%) | 3.46 | 3.63 | 3.52 | 4.22 |
| EPA, as % of fat in diet | — | 0.007 | 0.0005 | — |
| DHA, as % of fat in diet | — | 0.007 | 0.008 | — |
| 12:0, 14:0, and 16:0 as % | — | 0.013 | 0.006 | 0.139 |
| Total test fat in diet (%) | 0.000 | 0.272 | 0.038 | 0.236 |
| Phase 4 | | | | |
| Crude fat (%) | 3.54 | 3.71 | 3.59 | 4.31 |
| EPA, as % of fat in diet | — | 0.007 | 0.0005 | — |
| DHA, as % of fat in diet | — | 0.007 | 0.008 | — |
| 12:0 14:0, and 16:0 as % | — | 0.013 | 0.006 | 0.138 |
| Total test fat in diet (%) | 0.000 | 0.274 | 0.038 | 0.235 |

TABLE 10

The approximate calculated fatty acid balance of the grow-Finisher phase diets. Added fatty acids present were based on the total crude fat percentage and the DHA content match for both PUFA treatments to that in the Fertilium.

| | Treatment | | | |
|---|---|---|---|---|
| | Control | FERTILIUM ™ | aLDHA | Coconut |
| Phase 5 (nursery exit-45 kg) | | | | |
| Crude fat (%) | 3.55 | 3.73 | 3.61 | 4.32 |
| EPA, as % of fat in diet | — | 0.007 | 0.0005 | — |
| DHA, as % of fat in diet | — | 0.007 | 0.008 | — |
| 12:0, 14:0, and 16:0 as % of fat | — | 0.013 | 0.006 | 0.138 |
| Total test fat in diet (%) | 0.000 | 0.272 | 0.038 | 0.235 |
| Phase 6 (45-63 kg) | | | | |
| Crude fat (%) | 3.59 | 3.77 | 3.65 | 4.38 |
| EPA, as % of fat in diet | — | 0.007 | 0.0005 | — |
| DHA, as % of fat in diet | — | 0.007 | 0.008 | — |
| 12:0, 14:0, and 16:0 as % of fat | — | 0.013 | 0.006 | 0.138 |
| Total test fat in diet (%) | 0.000 | 0.274 | 0.038 | 0.236 |
| Phase 7 (63-82 kg) | | | | |
| Crude fat (%) | 3.63 | 3.80 | 3.68 | 4.42 |
| EPA, as % of fat in diet | — | 0.007 | 0.0005 | — |
| DHA, as % of fat in diet | — | 0.007 | 0.008 | — |
| 12:0, 14:0, and 16:0 as % of fat | — | 0.013 | 0.006 | 0.139 |
| Total test fat in diet (%) | 0.000 | 0.275 | 0.038 | 0.236 |
| Phase 8 (82-100 kg) | | | | |
| Crude fat (%) | 3.68 | 3.86 | 3.74 | 4.48 |
| EPA, as % of fat in diet | — | 0.007 | 0.0005 | — |
| DHA, as % of fat in diet | — | 0.007 | 0.008 | — |
| 12:0, 14:0, and 16:0 as % of fat | — | 0.013 | 0.006 | 0.139 |
| Total test fat in diet (%) | 0.000 | 0.274 | 0.038 | 0.236 |
| Phase 9 (>100kg) | | | | |
| Crude fat (%) | 3.73 | 3.92 | 3.79 | 4.55 |
| EPA, as % of fat in diet | — | 0.007 | 0.0005 | — |
| DHA, as % of fat in diet | — | 0.007 | 0.008 | — |
| 12:0, 14:0, and 16:0 as % of fat | — | 0.013 | 0.006 | 0.138 |
| Total test fat in diet (%) | 0.000 | 0.274 | 0.038 | 0.236 |

TABLE 11

Cumulative pig performance of gain (ADG), feed intake (ADFI) and feed conversion (FG) for pigs reared by sows fed differential sources of fatty acids in gestation + lactatation or to the piglet post weaning. Diets were crossed over from the nursery phase.

| Sow diet × Nursery/ Finisher diet Total Cumulative† | Dietary Treatment | | | | | | | | Significance | |
|---|---|---|---|---|---|---|---|---|---|---|
| | Control × Control | Fertilium × Coconut | Fertilium × Fertilium | DHA × Coconut | DHA × DHA | Coconut × Fertilium | Coconut × Coconut | SEM | Trt | Rep |
| ADG kg/d) | 0.50 | 0.51 | 0.51 | 0.52 | 0.51 | 0.52 | 0.52 | 0.007 | 0.28 | <0.0001 |
| ADFI (kg/d) | 1.21 | 1.23 | 1.22 | 1.23 | 1.22 | 1.27 | 1.26 | 0.019 | 0.27 | <0.0001 |
| F:G | 2.43 | 2.39 | 2.39 | 2.37 | 2.40 | 2.43 | 2.44 | 0.015 | 0.017 | <0.0001 |

†Denotes the period between weaning and market
ADG = average daily gain (kg/d), ADFI = average daily feed intake (kg/d), F:G = feed conversion ratio (feed to gain)

TABLE 12

The effect of continuous feeding of Fertilium ™ in gestation and lactation on subsequent litter size and piglet body weights.

| Response criteria | Control | FERTILIUM ™ | Pooled SEM | Diet P-value[1] |
|---|---|---|---|---|
| Subsequent litter | | | | |
| Sows, n[2] | 336 | 336 | — | — |
| Total born, n | 11.7 | 12.1 | 0.2 | 0.146 |
| Live born, n | 11.1 | 11.4 | 0.2 | 0.197 |
| Birth weight, lbs/pig | 3.82 | 3.81 | 0.04 | 0.906 |
| Weaning[3] | | | | |
| Piglets weaned, n | 9.5 | 10.0 | 0.2 | 0.066 |
| Weaning weight, lbs/pig | 12.15 | 12.53 | 0.12 | 0.026 |

[1]The main effect of diet was evaluated against the error term of diet × group interaction. Group refers to a farrowing room of 28 sows, half per treatment.
[2]There were a total of 24 groups of sows that had individual litter information.
[3]Due to cross-fostering and bump-weaning, piglets weaned (total of 24 groups with all information available) refers to the total number of piglets moved to the nursery divided by the total number of treatment litters farrowed, and weaning weight (total of 31 groups weaned) refers to the total pounds of pigs moved to the nursery divided by the total number of pigs moved within each treatment group.

TABLE 13

The effect of continuous feeding of Fertilium ™ on piglet body weights.

| Response criteria | Control | FERTILIUM ™ | Diet P-value |
|---|---|---|---|
| Sows, n | 77 | 88 | — |
| Standardized litter | | | |
| Litter size, n | 11.6 ± 0.2 | 11.5 ± 0.1 | 0.843 |
| Piglet weight, lbs | 3.76 | 3.76 | Covariable |
| d 14 litter | | | |
| Litter size, n | 10.4 ± 0.1 | 10.7 ± 0.1 | 0.130 |
| Piglet weight, lbs[1] | 9.66 ± 0.20 | 10.24 ± 0.19 | 0.05 |

[1]Including piglet weight at standardization as a covariable (means adjusted to 3.76 lb for both treatment groups)

TABLE 14

Fatty acid composition of jejunum samples obtained from piglets weaned from dams fed the control (Cont) and protected fish oil dietary regimens during gestation and(or) lactation (G/L).[1,2]

| Fatty acid | Cont/Cont | Cont/PFO | PFO/PFO | PFO/Cont |
|---|---|---|---|---|
| | (g/100 g) | | | |
| 14:0 | 0.06 | 0.09 | 0.05 | 0.10 |
| 16:0 | 19.82 | 19.31 | 20.13 | 21.52 |
| 16:1 | 1.45 | 1.27 | 1.24 | 1.17 |
| 18:0 | 22.14 | 25.86 | 23.28 | 20.03 |
| 18:1 | 13.43 | 12.31 | 11.64 | 14.60 |
| 18:2n6 | 21.65 | 20.28 | 20.25 | 20.05 |
| 18:3n6 | 0.25 | 0.16 | 0.24 | 0.24 |
| 18:3n-3 | 0.32 | 0.33 | 0.34 | 0.37 |
| 20:2 | 0.42 | 0.24 | 0.22 | 0.40 |
| 20:3n6 | 0.63 | 0.46 | 0.69 | 0.51 |
| 20:4n6 | 14.66 | 12.29 | 13.61 | 14.75 |
| 20:5n-3 | 0.18[a] | 0.73[b] | 0.74[b] | 0.25[a] |
| 22:4 | 1.82 | 1.27 | 1.17 | 1.94 |
| 22:5n-3 | 1.11[a] | 1.33[b] | 1.38[b] | 1.40[b] |
| 22:6n-3 | 0.27[a] | 3.68[b] | 4.51[b] | 2.15[a] |
| Other | 1.77 | 0.39 | 0.51 | 0.54 |
| Total | 100.00 | 100.00 | 100.00 | 100.00 |
| Saturated | 42.69 | 45.64 | 43.88 | 42.19 |
| n-3 | 2.88[a] | 6.06[c] | 6.97[c] | 4.17[b] |
| n6 | 37.20 | 33.20 | 34.79 | 35.54 |
| n6/n-3 | 12.91[a] | 5.47[b] | 5.16[b] | 8.81[b] |

[1]Means of four piglets per treatment.
[2]Within rows, means without a common letter differ, P < 0.05.

TABLE 15

Fatty acid composition of longissimus muscle samples obtained from piglets of dams weaned from dams fed the control (Cont) and protected fish oil (PFO) dietary regimens during gestation and(or) lactation (G/L).[1,2]

| Fatty acid | Cont/Cont | Cont/PFO | PFO/PFO | PFO/Cont |
|---|---|---|---|---|
| | (g/100g fatty acids) | | | |
| 14:0 | 0.25 | 0.22 | 0.16 | 0.51 |
| 16:0 | 21.41 | 21.23 | 20.64 | 20.48 |
| 16:1 | 2.68 | 2.55 | 2.44 | 3.43 |
| 18:0 | 15.77 | 15.22 | 14.59 | 15.82 |
| 18:1 | 13.51 | 12.92 | 14.94 | 17.79 |
| 18:2n6 | 26.92 | 25.45 | 23.76 | 23.46 |
| 18:3n6 | 0.00 | 0.00 | 0.08 | 0.00 |
| 18:3n-3 | 0.39 | 0.36 | 0.32 | 0.39 |
| 20:2 | 0.61 | 0.59 | 0.63 | 0.68 |
| 20:3n6 | 1.05 | 1.09 | 0.93 | 1.02 |
| 20:4n6 | 13.32 | 12.20 | 12.43 | 12.18 |
| 20:5n-3 | 0.34 | 0.98 | 3.29 | 0.30 |
| 22:4 | 2.14 | 1.55 | 1.48 | 1.71 |
| 22:5n-3 | 1.52 | 1.87 | 1.83 | 1.44 |
| 22:6n-3 | 0.00[a] | 1.97[b] | 2.48[b] | 0.70[c] |
| Other | 0.09 | 0.00 | 0.00 | 0.10 |

TABLE 15-continued

Fatty acid composition of longissimus muscle samples obtained from piglets of dams weaned from dams fed the control (Cont) and protected fish oil (PFO) dietary regimens during gestation and(or) lactation (G/L).[1,2]

| Fatty acid | Cont/Cont | Cont/PFO | PFO/PFO | PFO/Cont |
|---|---|---|---|---|
| | (g/100g fatty acids) | | | |
| Total | 100.00 | 100.00 | 100.00 | 100.07 |
| Saturated | 37.43 | 38.47 | 35.39 | 36.81 |
| n-3 | 2.25[a] | 5.18[bc] | 7.92[b] | 2.84[ac] |
| n6 | 41.29 | 38.74 | 37.20 | 36.65 |
| n6/n-3 | 18.64[a] | 7.55[b] | 5.89[b] | 14.42[a] |

[1]Means of four piglets per treatment.
[2]Within rows, means without a common letter differ, $P < 0.05$.

What is claimed is:

1. A method of increasing the performance of an animal, the method comprising the steps of
administering to the animal a feed composition comprising an algal composition comprising omega-3 fatty acids or esters thereof, wherein the omega-3 fatty acids comprise docosahexaenoic acid and eicosapentaenoic acid, wherein the ratio of docosahexaenoic acid to eicosapentaenoic acid in the algal composition is about 60:1 to about 1:1, wherein the feed composition as a final mixture comprises about 0.01% to about 60% by weight of the algal composition, and wherein the animal is a species of poultry; and
increasing the performance of the animal.

2. The method of claim 1 wherein the feed composition as a final mixture comprises about 0.01% to about 4.0% by weight of the algal composition.

3. The method of claim 1 wherein the feed composition as a final mixture comprises about 0.01% to about 3.0% by weight of the algal composition.

4. The method of claim 1 wherein the feed composition as a final mixture comprises about 0.01% to about 1.5% by weight of the algal composition.

5. The method of claim 1 wherein the animal is a chicken.

6. The method of claim 1 wherein the feed composition as a final mixture further comprises omega-6 fatty acids or esters thereof.

7. The method of claim 1 wherein the feed composition is administered daily to the animal.

8. The method of claim 1 wherein the feed composition as a final mixture further comprises an antioxidant.

9. The method of claim 1 wherein the ratio of docosahexaenoic acid to eicosapentaenoic acid is about 10:1.

10. The method of claim 1 wherein the ratio of docosahexaenoic acid to eicosapentaenoic acid is about 5:1.

11. The method of claim 1 wherein the ratio of docosahexaenoic acid to eicosapentaenoic acid is about 2:1.

12. The method of claim 1 wherein the ratio of docosahexaenoic acid to eicosapentaenoic acid is about 1:1.

13. The method of claim 1 wherein the animal is a chick.

14. The method of claim 1 wherein the omega-3 fatty acids in the feed composition are stabilized by encapsulation.

* * * * *